United States Patent
Harris et al.

(10) Patent No.: US 10,758,270 B2
(45) Date of Patent: Sep. 1, 2020

(54) SURGICAL TOOL STABILIZATION DEVICES FOR TROCAR ASSEMBLIES

(71) Applicant: Ethicon LLC, Guaynabo, PR (US)

(72) Inventors: Jason Harris, Mason, OH (US); Joshua Young, Loveland, OH (US); Stephanie Toy, Cincinnati, OH (US); Jerry Morgan, Cincinnati, OH (US)

(73) Assignee: Ethicon LLC, Guaynabo, PR (US)

(*) Notice: Subject to any disclaimer, the term of this patent is extended or adjusted under 35 U.S.C. 154(b) by 259 days.

(21) Appl. No.: 15/727,107

(22) Filed: Oct. 6, 2017

(65) Prior Publication Data

US 2019/0105076 A1    Apr. 11, 2019

(51) Int. Cl.
*A61B 17/34* (2006.01)
*A61B 1/313* (2006.01)

(52) U.S. Cl.
CPC ...... *A61B 17/3462* (2013.01); *A61B 17/3417* (2013.01); *A61B 17/3423* (2013.01); *A61B 17/3439* (2013.01); *A61B 1/3132* (2013.01); *A61B 17/3498* (2013.01); *A61B 2017/347* (2013.01); *A61B 2017/3441* (2013.01); *A61B 2017/3464* (2013.01)

(58) Field of Classification Search
CPC ............ A61B 17/3417; A61B 17/3423; A61B 17/3439; A61B 17/3498; A61B 2017/347; A61B 17/3462; A61B 2017/3464; A61B 2017/348; A61B 2017/3441
See application file for complete search history.

(56) References Cited

U.S. PATENT DOCUMENTS

| 5,603,702 A | * | 2/1997 | Smith | A61B 17/3462 251/149.1 |
| 6,224,608 B1 | * | 5/2001 | Ciccolella | A61B 17/3421 604/115 |
| 8,202,252 B2 | | 6/2012 | Ross | |
| 2008/0294112 A1 | * | 11/2008 | Judson | A61B 17/3462 604/167.06 |
| 2009/0076456 A1 | | 3/2009 | Armstrong et al. | |
| 2010/0286706 A1 | | 11/2010 | Judson et al. | |
| 2012/0116313 A1 | | 5/2012 | Franer et al. | |
| 2015/0196322 A1 | * | 7/2015 | Sauter | A61B 17/3462 604/167.06 |
| 2015/0342593 A1 | * | 12/2015 | Lauchner | A61B 17/0293 600/245 |

FOREIGN PATENT DOCUMENTS

| WO | 9417844 A1 | 8/1994 |
| WO | 0189397 A1 | 11/2001 |
| WO | 2011082114 A1 | 7/2011 |

OTHER PUBLICATIONS

ISRWO of corresponding PCT/IB2018/057469 dated Dec. 10, 2018.

* cited by examiner

*Primary Examiner* — Katrina M Stransky
(74) *Attorney, Agent, or Firm* — Vorys, Sater, Seymour and Pease LLP

(57) ABSTRACT

A trocar assembly includes a trocar housing that defines a working chamber, and a cannula coupled to the trocar housing at a proximal end to facilitate communication between the cannula and the working chamber. A tool stabilizing device is coupled to at least one of the trocar housing and the cannula and is actuatable to stabilize and center a surgical tool within the cannula.

19 Claims, 16 Drawing Sheets

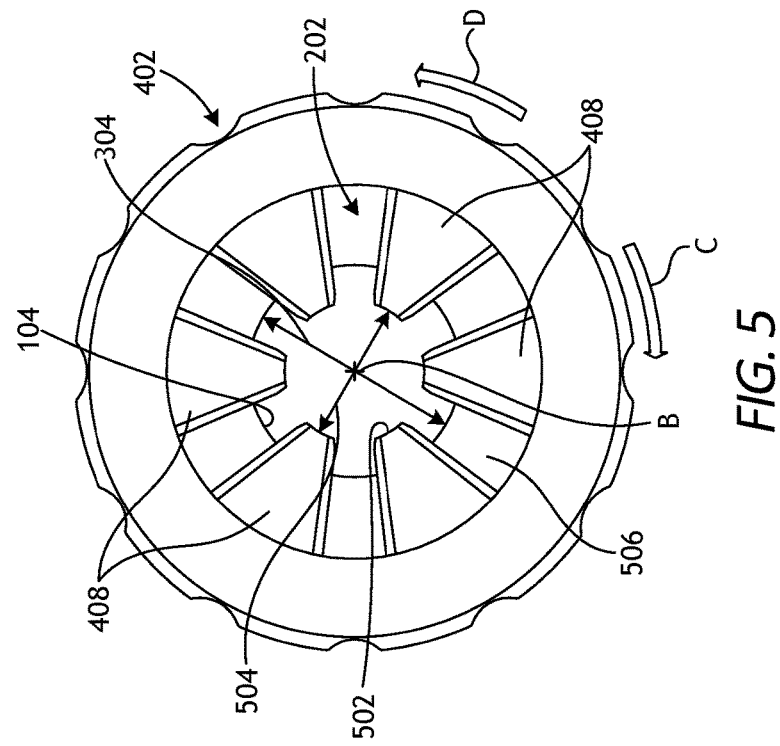
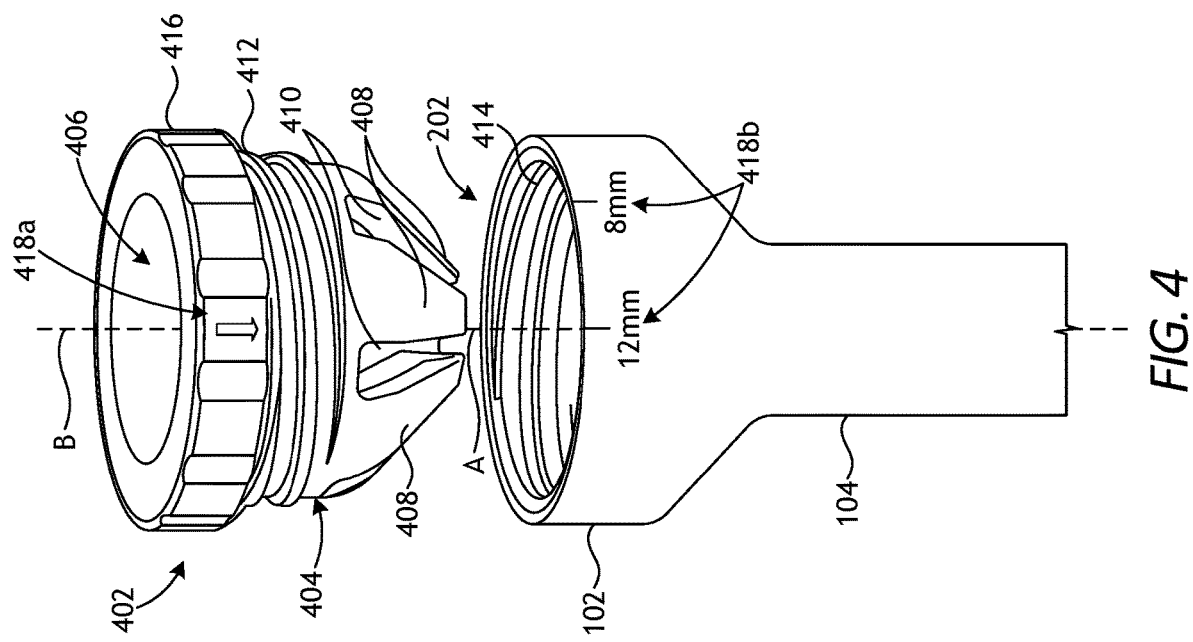
FIG. 5
FIG. 4

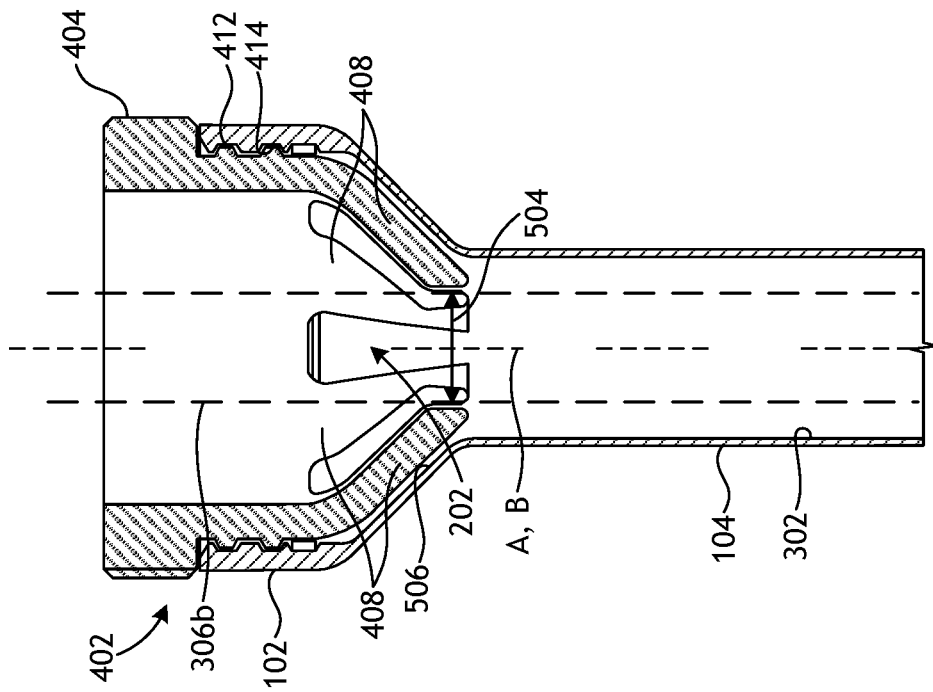
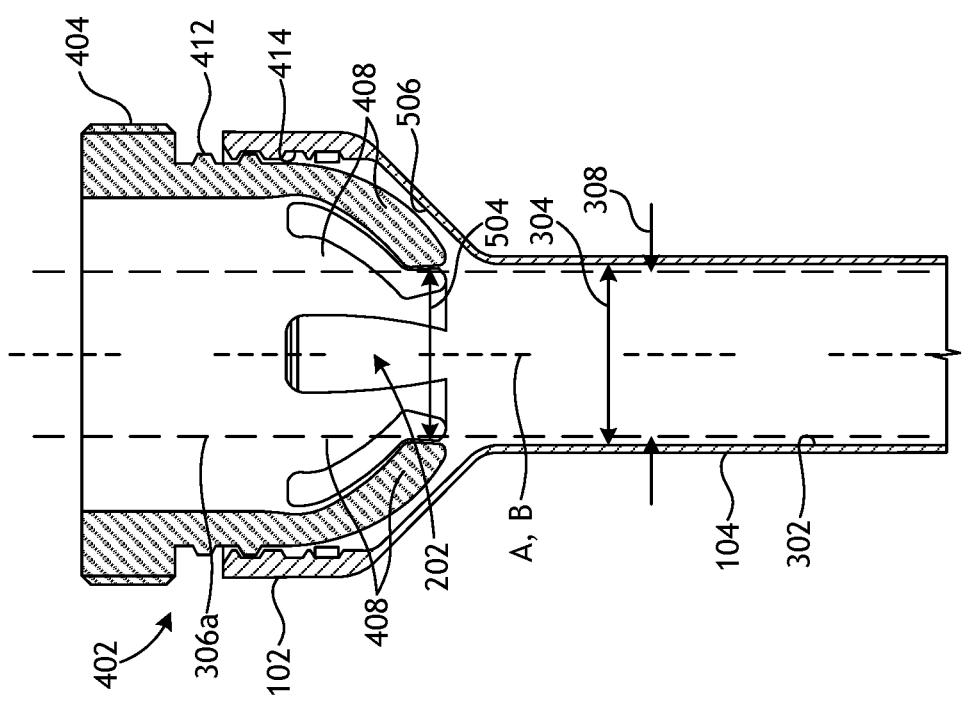

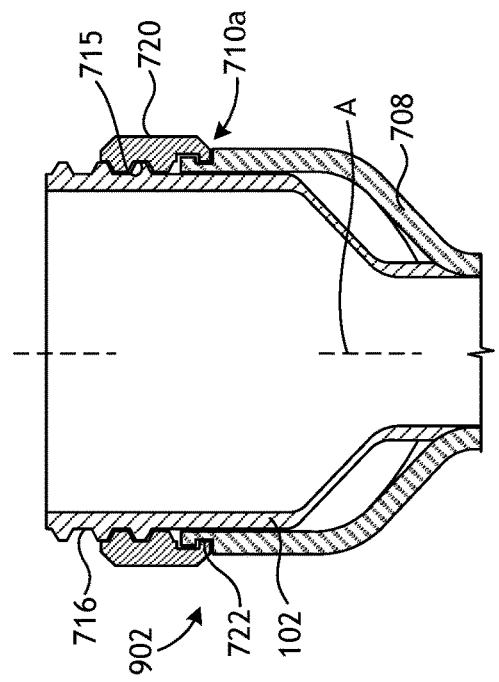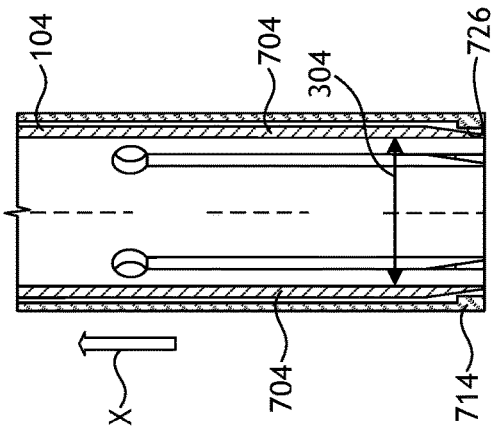
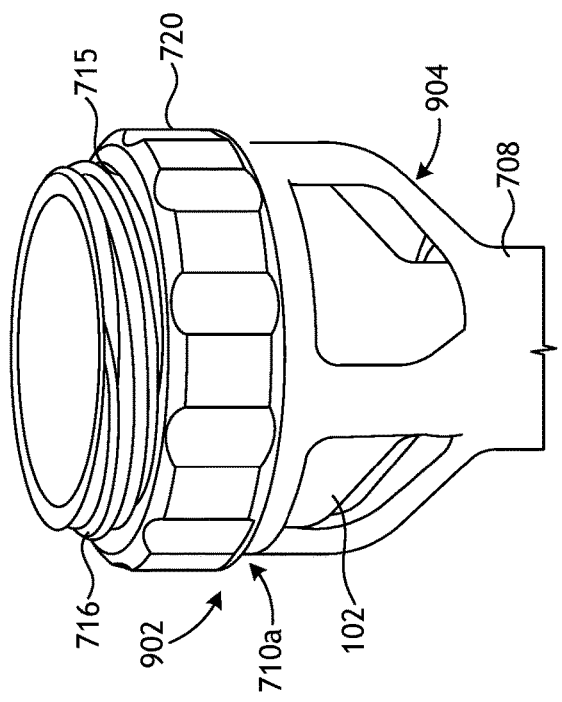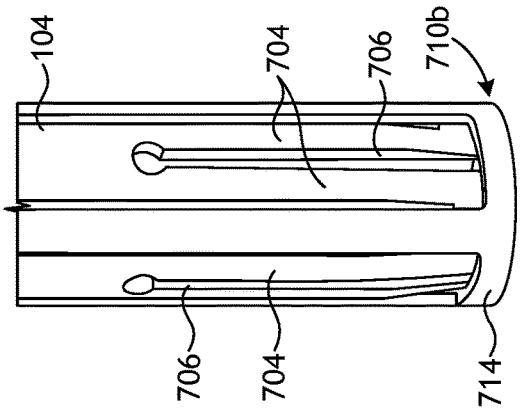
FIG. 9A
FIG. 9B

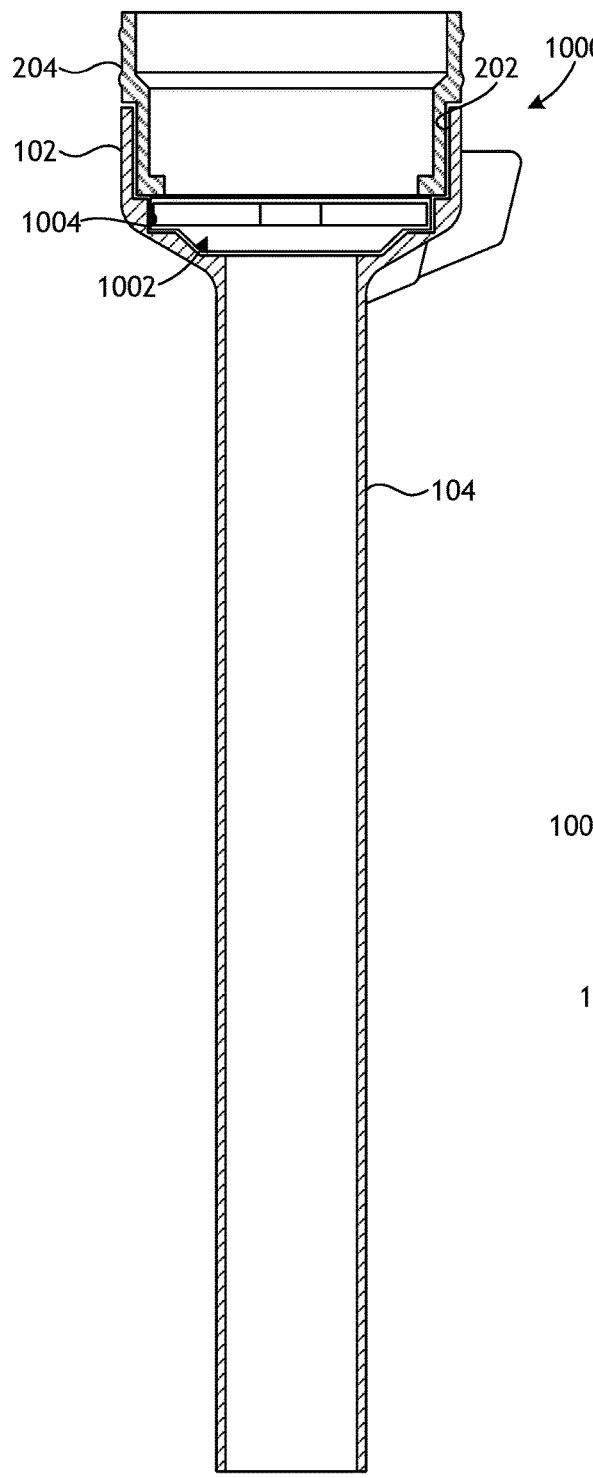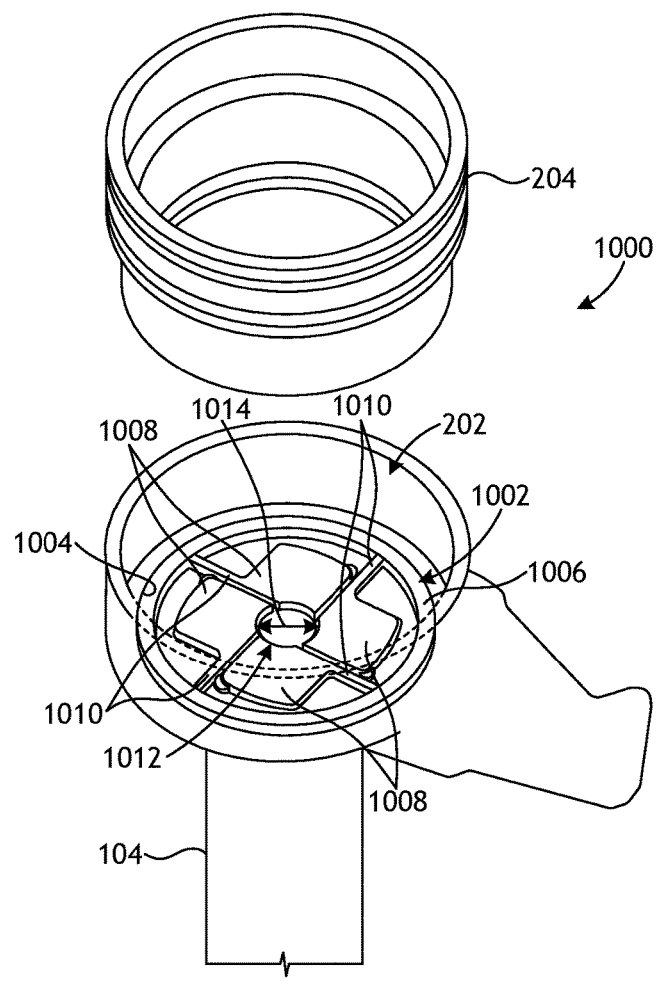
FIG. 10A
FIG. 10B

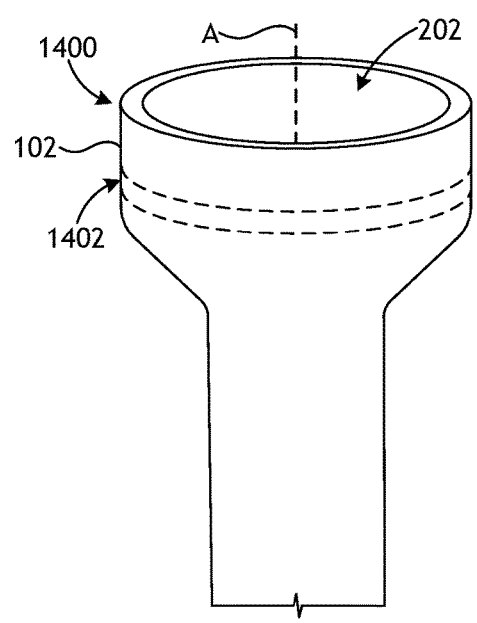
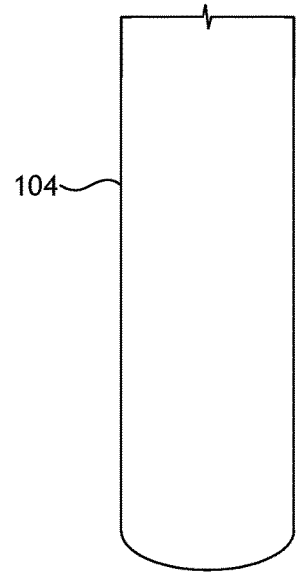
FIG. 14
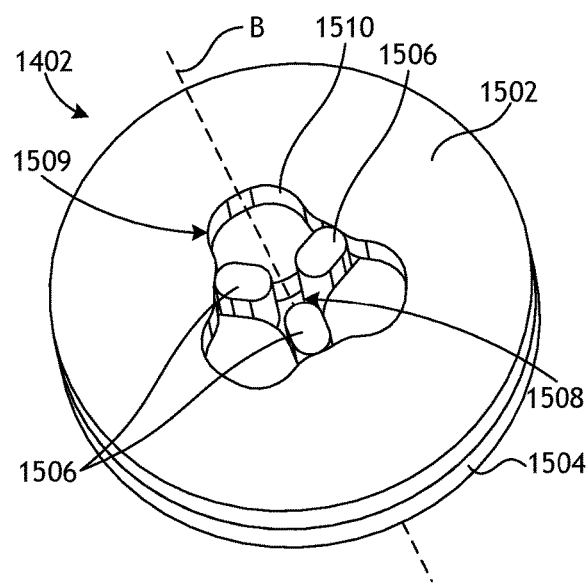
FIG. 15A
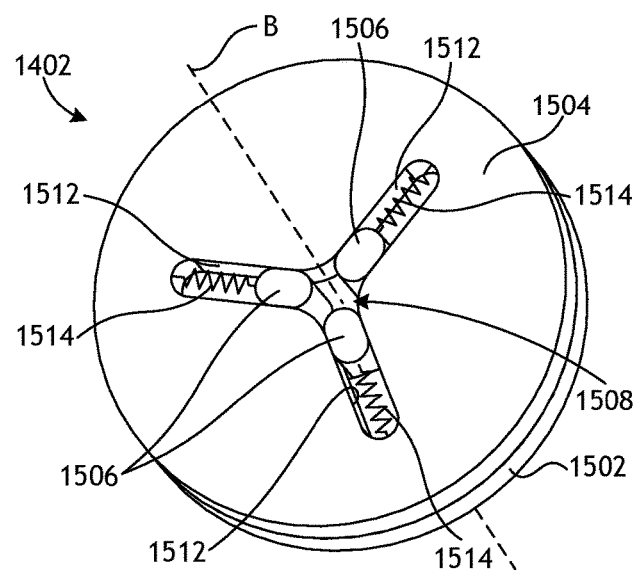
FIG. 15B

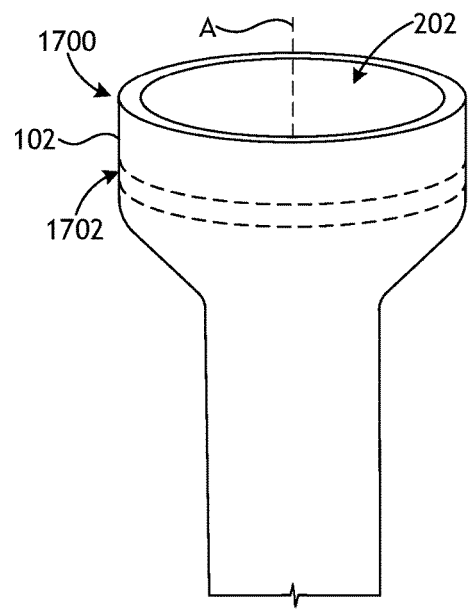
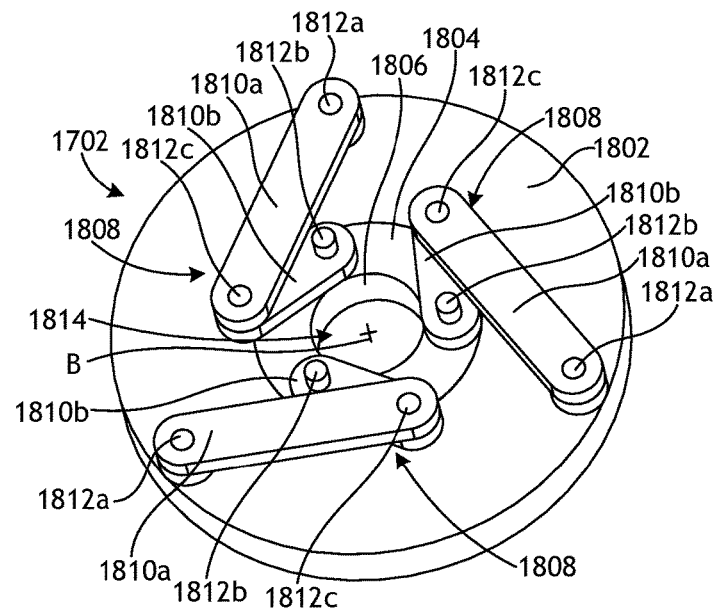
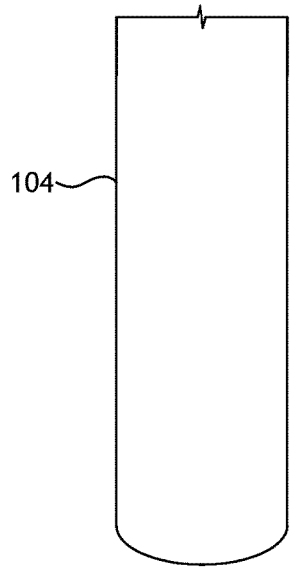
FIG. 17
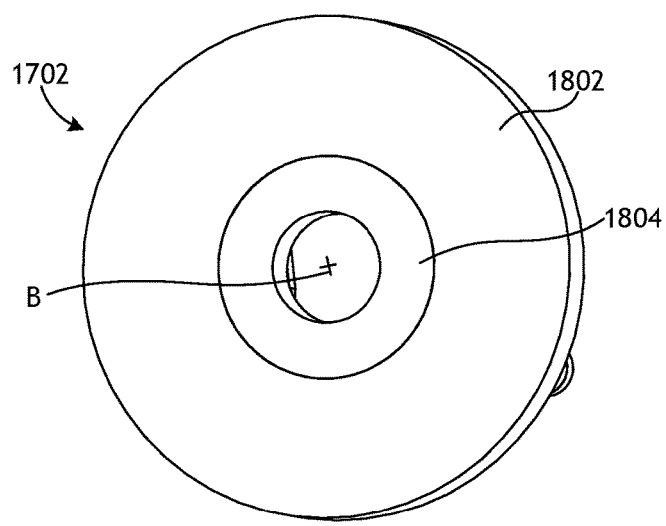
FIG. 18A
FIG. 18B

SURGICAL TOOL STABILIZATION DEVICES FOR TROCAR ASSEMBLIES

BACKGROUND

During laparoscopic surgery, one or more small incisions are formed in the skin of a patient and a trocar assembly is inserted through the incision to form a pathway that provides access to an internal body cavity, such as the patient's abdomen. The trocar assembly is used to introduce various instruments and tools into the abdomen, as well as to provide insufflation that elevates interior walls of the abdomen.

A trocar assembly generally includes a housing, a cannula that extends from the housing, and an obturator that can be inserted into the housing and the cannula. To set the trocar assembly for a surgical operation, the obturator is extended through an interior lumen of the cannula, at which point the obturator may penetrate the patient's skin to access the abdominal cavity. To penetrate the skin, the distal end of the cannula is placed against an incision in the skin and pressure is applied to the proximal end of the trocar to force the sharp point of the obturator through the skin until it enters a targeted location in the abdominal cavity. The obturator can then be withdrawn, leaving the interior lumen of the cannula as a path to access the abdominal cavity from outside the body.

The trocar housing is attached to the proximal end of the cannula and defines a working chamber with an open distal end in communication with the interior lumen of the cannula. Just as the interior lumen can receive the obturator, it is also sized to receive elongated surgical tools that are axially extended into and withdrawn from the cannula through the proximal end portion of the working chamber.

For surgical operations, a surgeon will normally use a 1:1 pairing of a trocar assembly and a surgical tool based on size (diameter). For example, if an 8 mm (diameter) surgical tool is required for an operation, a corresponding 8 mm (diameter) trocar assembly will normally be used. In robotic surgery, however, trocar assemblies and surgical tools do not always enjoy a 1:1 pairing. For example, 12 mm (diameter) trocar assemblies are typically used in robotic surgery, which enables use of 12 mm (diameter) surgical tools, such as a surgical stapler. For some procedures, however, an 8 mm or 5 mm (diameter) surgical tool may be required and will have to pass through the same 12 mm trocar assembly.

When the trocar assembly and surgical tool pairing is not 1:1, the tip (distal end) of the surgical tool is prone to various types of unintended motion, such as deflection, oscillation in place, and spring back oscillation. Unintended tip motion can lead to the instrument contacting or damaging tissues in a manner contrary to the intent of the surgeon. These events resulting from unintended motion can produce adverse clinical impacts. For instance, unintended lacerations or other tissue damage may require additional surgical intervention or even permanent tissue damage.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 4 depicts an exploded isometric view of an example tool stabilizing device that may be incorporated into the trocar assembly of FIGS. 1-3.

FIG. 5 is a top end view of the tool stabilizing device of FIG. 4.

FIGS. 6A and 6B are cross-sectional side views of the tool stabilizing device of FIG. 4 during example operation.

FIG. 9A is an isometric view of another example tool stabilizing device that may be incorporated into the trocar assembly of FIGS. 1-3.

FIG. 9B is a cross-sectional side view of the tool stabilizing device of FIG. 9A used in conjunction with the housing and the cannula.

FIG. 10A is a cross-sectional view of a trocar assembly incorporating another example tool stabilizing device.

FIG. 10B is a partial exploded view of the trocar assembly of FIG. 10A.

FIG. 14 is a cross-sectional view of a trocar assembly incorporating another example tool stabilizing device.

FIGS. 15A and 15B are top and bottom isometric views, respectively, of an example embodiment of the tool stabilizing device of FIG. 14.

FIG. 17 is a cross-sectional view of a trocar assembly incorporating another example tool stabilizing device.

FIGS. 18A and 18B are top and bottom isometric views, respectively, of an example embodiment of the tool stabilizing device of FIG. 17.

DETAILED DESCRIPTION

The present disclosure is related to trocar assemblies and, more particularly, to tool stabilizing devices used to center surgical tools within a trocar cannula of a trocar assembly and mitigate unwanted oscillation and vibration.

The embodiments described herein provide several variations, configurations, and designs of tool stabilizing devices that can be incorporated into a trocar assembly to help stabilize and center surgical tools of a variety of sizes. The tool stabilizing devices may be selectively actuatable to accommodate surgical tools having a range of outer diameters. In some embodiments, the tool stabilizing devices may be manually actuated, but can alternatively be autonomously actuated, actuated using a robot or another automated actuation system, or any combination thereof.

Figure 1:
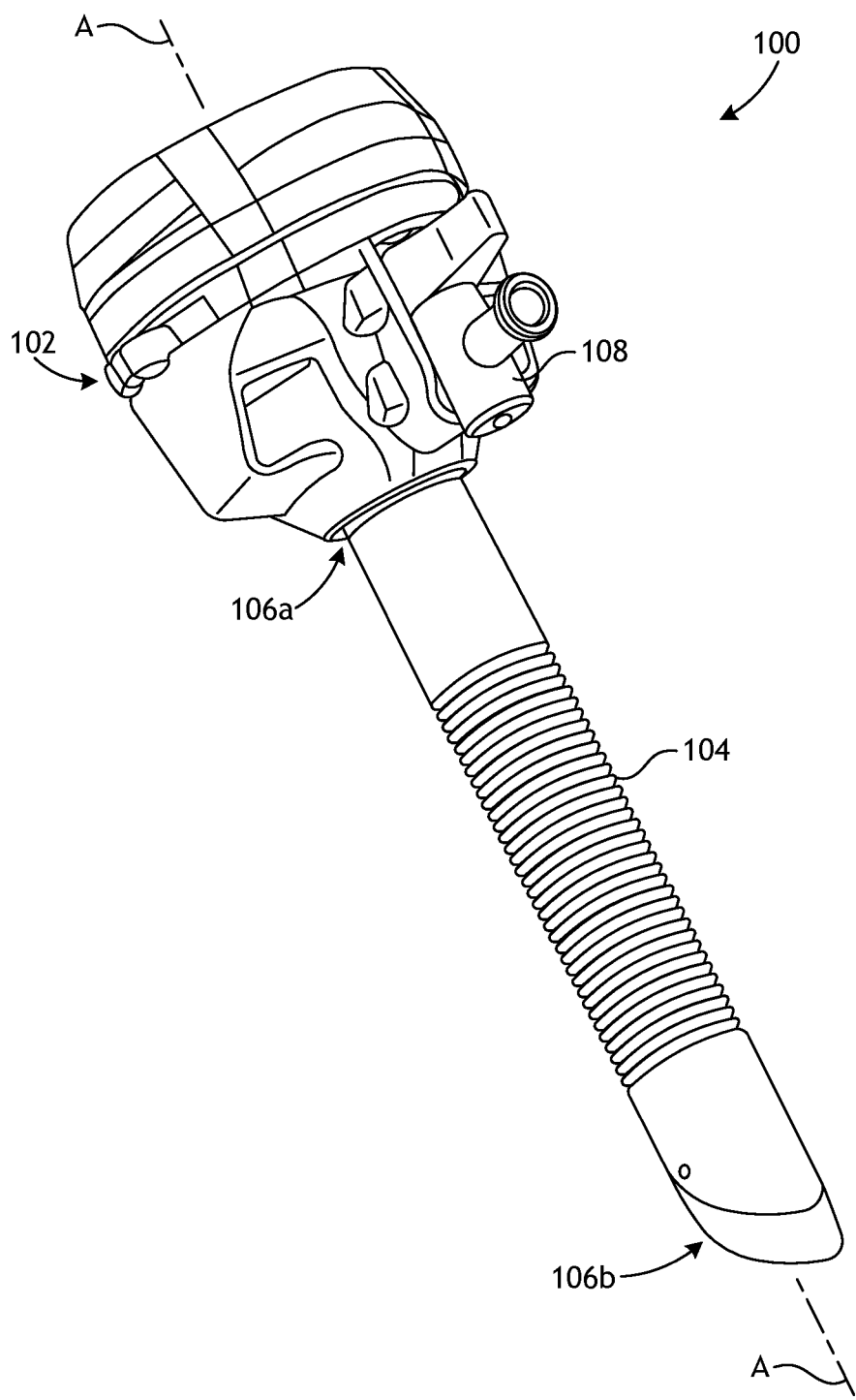
FIG. 1 is an isometric view of an example trocar assembly that may incorporate the principles of the present disclosure.

FIG. 1 is an isometric view of an example trocar assembly 100 that may incorporate the principles of the present disclosure. The depicted trocar assembly 100 is just one example trocar assembly that can suitably incorporate the principles of the present disclosure. Indeed, many alternative designs and configurations of the trocar assembly 100 may be employed, without departing from the scope of this disclosure.

As illustrated, the trocar assembly 100 includes a trocar housing 102 and a cannula 104. The cannula 104 has a proximal end 106a and a distal end 106b. The cannula 104 is coupled to the trocar housing 102 at the proximal end 106a and extends distally therefrom. In some embodiments, the cannula 104 may comprise an integral extension of the trocar housing 102. In other embodiments, however, the trocar housing 102 and the cannula 104 may comprise two separate components that are mated to one another. The trocar housing 102 and cannula 104 may be made of any rigid or semi-rigid material, such as a metal or a plastic.

The trocar assembly 100 may also include an insufflation valve 108 (e.g., a stopcock valve) coupled to the trocar housing 102 or forming an integral part thereof. The insufflation valve 108 is operable to introduce an insufflation fluid (e.g. carbon dioxide) through the trocar housing 102 and the cannula 104 and subsequently into an inner cavity (e.g., the abdomen) of a patient to elevate the interior walls of the inner cavity. While not shown, the trocar assembly 100 may also include an obturator extendable through the trocar assembly along a centerline A of the trocar assembly 100. When used, the obturator extends through the cannula 104 and out the distal end 106b to penetrate a patient's skin and thereby facilitate access to the abdominal cavity.

Figure 2:
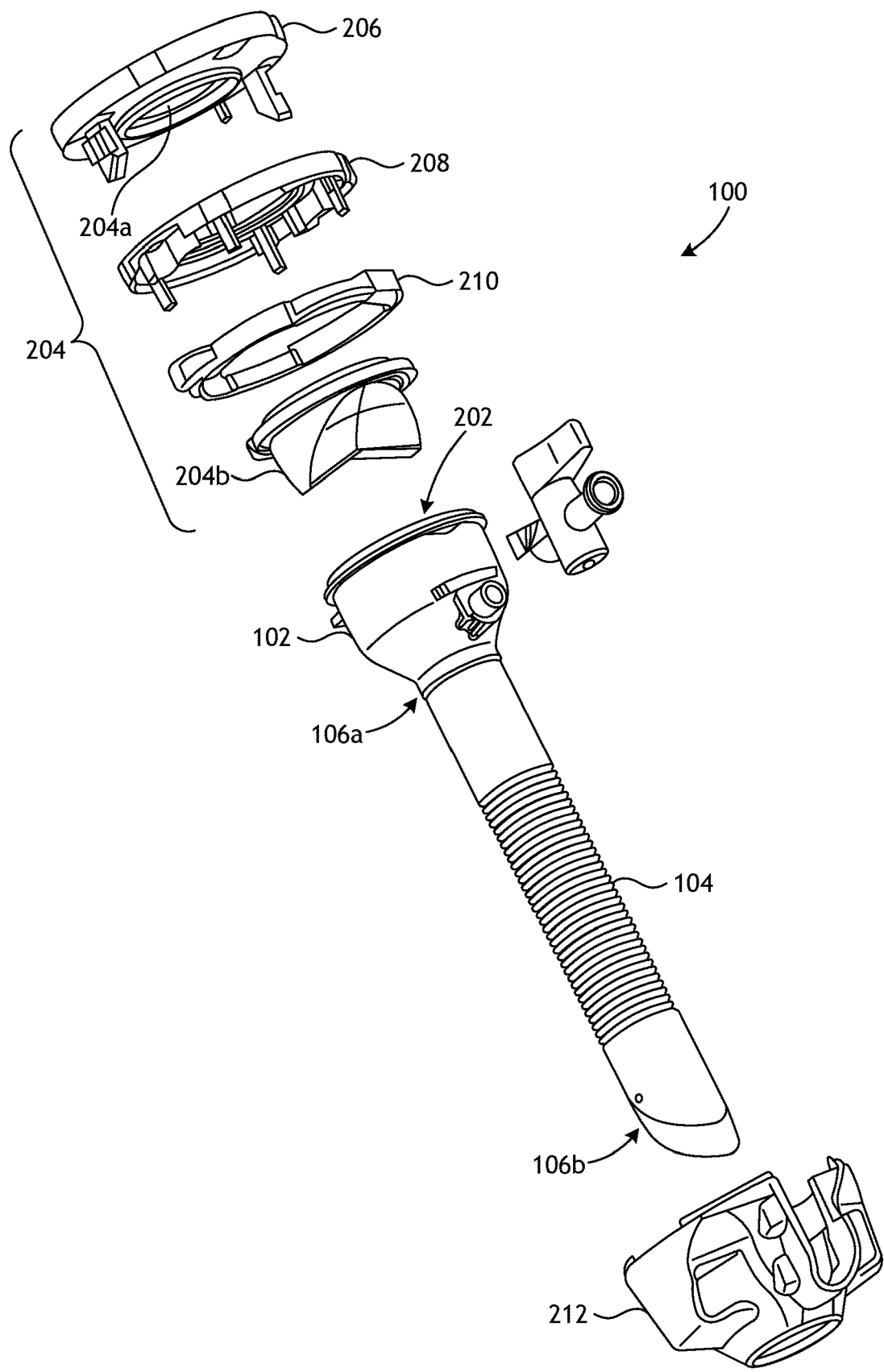
FIG. 2 is an exploded view of the trocar assembly of FIG. 1.

FIG. 2 is an exploded view of the trocar assembly 100 of FIG. 1. The trocar housing 102 provides and otherwise defines a working chamber 202 that communicates with a lumen defined within the cannula 104. The lumen is open-ended and extends between the proximal and distal ends 106a,b of the cannula 104.

The working chamber 202 is also open-ended and configured to at least partially receive a seal cartridge 204 that includes a first or "proximal" seal assembly 204a and a second or "distal" seal assembly 204b. The first and second seal assemblies 204a,b allow selective sealing of the working chamber 202 during operation. In at least one embodiment, as illustrated, the second seal assembly 204b may comprise a duckbill seal. While two seal assemblies 204a,b are depicted in FIG. 2, the seal cartridge 204 may alternatively include more or less than two seal assemblies, without departing from the scope of the disclosure.

The seal assemblies 204a,b may be made of an elastic or pliable material. Suitable elastic or pliable materials include, but are not limited to, rubber (e.g., natural rubber, synthetic rubber, nitrile rubber, silicone rubber, a urethane rubber, a polyether rubber, chloroprene rubber, ethylene propylene diene monomer, styrene-butadiene rubber, etc.), silicone, ethylene vinyl acetate, nylon, vinyl, spandex, polyurethane, polyethylene, polypropylene, polyisoprene, or any combination thereof. Examples of seal cartridges are described in U.S. Pat. No. 8,771,307, the contents of which are hereby incorporated by reference.

The seal cartridge 204 may be assembled in a variety of ways. In the illustrated embodiment, for example, a crown ring 206 and a gasket ring 208 may be snap-fit together, and a gasket retainer ring 210 may be configured to secure an attachment between the gasket ring 208 and the trocar housing 102. A housing retainer 212 may then be extended about the exterior of the trocar housing 102 to secure the internal components to the trocar housing 102. These components may be made of any rigid or semi-rigid biocompatible material, such as a metal or a plastic.

Figure 3:
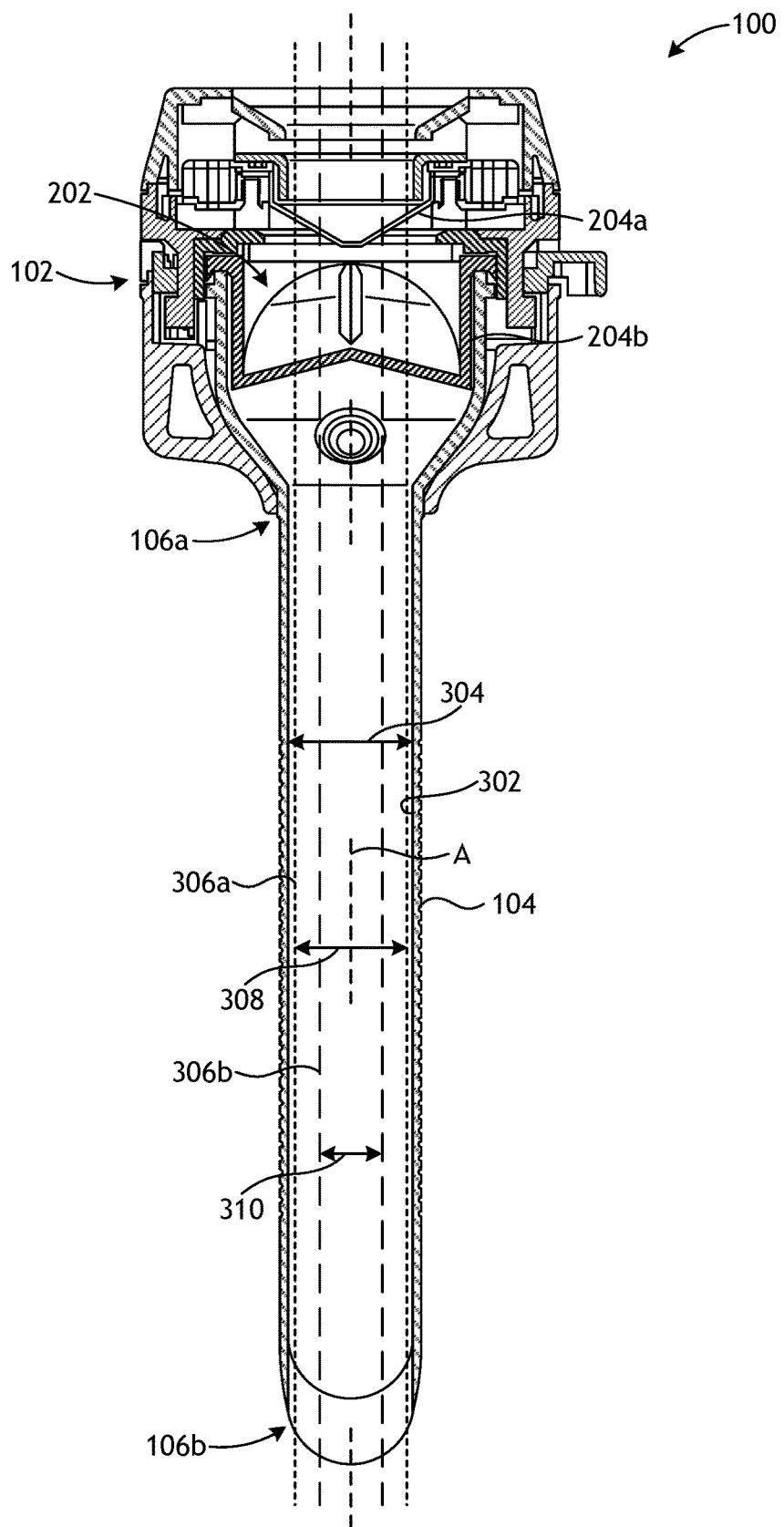
FIG. 3 is a cross-sectional side view of the trocar assembly of FIG. 1.

FIG. 3 is a cross-sectional side view of the trocar assembly 100. As illustrated, the cannula 104 defines and otherwise provides a lumen 302 that extends between the proximal and distal ends 106a,b and communicates with the working chamber 202 provided by the trocar housing 102. The lumen 302 exhibits an inner diameter 304 configured to receive surgical tools having an outer diameter equal to (i.e., slightly less than equal) or less than the inner diameter 304.

In at least one embodiment, the inner diameter 304 may be sized to receive a 12 mm surgical tool. In such embodiments, the trocar assembly 100 may be referred to and otherwise characterized as a "12 mm trocar," which is commonly used in robotic surgery to accommodate various 12 mm surgical tools, such as surgical staplers. In the illustrated embodiment, a first surgical tool 306a (depicted in dashed lines) extends through the trocar assembly 100 and projects out each end. While not explicitly shown, the first and second seal assemblies 204a,b are configured to deform and provide a sealed interface against the outer surface of the first surgical tool 306a as the first surgical tool 306a is extended into the trocar assembly 100.

The first surgical tool 306a exhibits an outer diameter 308 of approximately 12 mm, which is slightly smaller than the inner diameter 304 of the lumen 302. Accordingly, the first surgical tool 306a may be referred to as a "12 mm surgical tool" and the lumen 302 is sized to receive the first surgical tool 306a such that very little space (e.g., less than 1 mm) remains between the inner and outer diameters 304, 308. Consequently, the first surgical tool 306a is generally centered within the cannula 302 along the centerline A at all times, which tends to mitigate unwanted occurrences of deflection, oscillation, and vibration of the first surgical tool 306a.

At times, however, surgical tools smaller than first surgical tool 306a may need to be introduced into the trocar assembly 100 to perform additional procedures. In the illustrated embodiment, for example, a second surgical tool 306b (depicted in dashed lines) extends through the trocar assembly 100 and projecting out each end. Similar to the first surgical tool 306a, as the second surgical tool 306b is extended into the trocar assembly 100, the first and second seal assemblies 204a,b are configured to deform and provide a sealed interface against the outer surface of the second surgical tool 306b.

The second surgical tool 306b exhibits an outer diameter 310 that is smaller than the outer diameter 308 of the first surgical tool 306a, and smaller than the inner diameter 304 of the lumen 302. In some applications, for example, the outer diameter 310 may be approximately 8 mm. In such applications, the second surgical tool 306b may be referred to as an "8 mm surgical tool." Alternatively, the outer diameter 310 may be approximately 5 mm, and the second surgical tool 306b may instead be referred to as a "5 mm surgical tool."

Since the outer diameter 310 of the second surgical tool 306b is much smaller than the inner diameter 304 of the lumen 302, the second surgical tool 306b will rarely (if ever) be centered within the cannula 302 along the centerline A during operation. Rather, during operation the second surgical tool 306b will be prone to deflection, oscillation in place, spring back oscillation, and vibration as the second surgical tool 306b is manipulated in various directions. Such unintended motion of the second surgical tool 306b can lead to the instrument inadvertently contacting or damaging tissues contrary to the intent of the surgeon. These types of motion can also each have an adverse clinical impact as lacerations or other damage to tissue that is not intended by the surgeon can require additional intervention or uncorrectable issues with the tissue.

According to embodiments of the present disclosure, the trocar assembly 100 may incorporate a tool stabilizing device that is selectively actuatable to adjust the effective inner diameter of the cannula 104 and thereby eliminate or significantly minimize unintended oscillation movement and vibration of smaller surgical tools, e.g., the second surgical tool 306b. That is, the tool stabilizing device may allow the second surgical tool 306b to be centered or stabilized more effectively within the lumen 302. The tool stabilizing device may be manually actuated, autonomously actuated, actuated using a robot or another automated actuation system, or any combination thereof.

FIG. 4 is an exploded isometric view of an example tool stabilizing device 402 that may be incorporated into the trocar assembly 100 of FIGS. 1-3, according to one or more embodiments of the present disclosure. In the illustrated embodiment, the tool stabilizing device 402 (hereafter "the device 402") may comprise a generally annular body 404 sized and otherwise configured to be received into the working chamber 202 of the trocar housing 102. The body 404 may have a centerline B that is substantially coaxial with the centerline A of the cannula 104 when the device 402 is properly received within the working chamber 202.

In some embodiments, the body 404 may comprise the seal cartridge 204 of FIG. 2 and the seal assemblies 204a,b (FIG. 2) may be received within an interior 406 of the body 404. In other embodiments, however, the body 404 may merely form a part of the seal cartridge 204. In yet other embodiments, the body 404 may comprise an entirely separate structure independent of the seal cartridge 204, without departing from the scope of the disclosure. In such embodiments, the seal cartridge 204 and the associated seal assemblies 204a,b may be received within the interior 406 of the body 404.

As illustrated, the body 404 may provide a plurality of longitudinal (elongated) fingers 408 that extend distally from the body 404 and are separated by a corresponding plurality of elongated slots 410. The fingers 408 may extend radially inward and toward the centerline B of the body 404, thereby jointly forming a generally frustoconical shape configured to interact with an opposing generally frustoconical inner surface (or profile) defined within the working chamber 202 of the housing 102.

In some embodiments, the body 404 may be threaded to the housing 102. More specifically, the body 404 may provide a series of external threads 412 configured to mate with an opposing series of internal threads 414 defined within the working chamber 202 and, more particularly, on an inner radial surface of the working chamber 202. As will be appreciated, design modifications to the body 404 may result in the threads 412 being arranged internally to the body 404 and the threads 414 being arranged externally to the housing 102, without departing from the scope of the disclosure.

The device 402 may be actuated to help center and stabilize surgical tools of varying diameters that may be introduced into the cannula 104. Actuating the presently illustrated device 402, for example, comprises rotating the body 404 relative to the housing 102 and the cannula 104 via the threaded interface provided by the opposing threads 412, 414. Depending on the angular direction, rotating (actuating) the device 402 about the centerline B advances the body 404 into or out of the working chamber 202. As the body 404 advances into the working chamber 202, the fingers 408 will eventually engage the frustoconical inner surface (or profile) within the working chamber 202. Advancing the body 404 against the frustoconical inner surface urges the fingers 408 to flex radially inward and thereby reduce an inner diameter between the distal termini of the fingers 408. Withdrawing the body 404 from the working chamber 202 allows the fingers 408 to retract back to their natural state, and return the inner diameter between the termini of the fingers 408 back to its relaxed state.

Reducing the inner diameter of the fingers 408 may prove advantageous in helping support and center smaller-diameter surgical tools within the cannula 104. In some embodiments, the pitch of the opposing threads 412, 414 may be designed such that a predetermined amount of rotation of the device 402 changes the inner diameter between the termini of the fingers 408 to a predetermined magnitude (e.g., 12 mm, 8 mm, 5 mm, etc.). Accordingly, a user may be able to selectively actuate the device 402 to accommodate, stabilize, and center surgical tools of a variety of sizes within the cannula 104.

In at least one embodiment, the device 402 may be actuated manually. More specifically, the body 404 may include a gripping interface 416, which may provide a location for a user (i.e., a surgeon or clinician) to grasp and manually rotate (actuate) the device 402 about the centerline B relative to the housing 102. In other embodiments, however, actuation of the device 402 may be automated, such as with a motor (not shown) or a robot that includes an actuation arm (not shown) that may be attached to the device 402, such as at the gripping interface 416. In such embodiments, the motor or robotic actuation arm may be configured to rotate the body 404 about the centerline B to advance the body 404 into and out of the working chamber 202. In yet other embodiments, the device 402 may be actuated through a combination of manual and automated actuation, without departing from the scope of the disclosure.

In some embodiments, device 402 may include markings to help a user visually track the rotational progress of the device 402 during actuation. In the illustrated embodiment, for example, a first marking 418a may be included on the gripping interface 416 and configured to align with a plurality of second markings 418b provided on the housing 102, for example. The first and second markings 418a,b may be strategically positioned in conjunction with a predetermined pitch of the opposing threads 412, 414. During actuation, the body 404 might be rotated to align with a 12 mm marking 418b, which indicates that the device 402 may be positioned to receive and stabilize a 12 mm surgical tool. The body 404 might alternatively be rotated to an 8 mm marking 418b, which indicates that the device 402 may be positioned to receive and stabilize an 8 mm surgical tool. As will be appreciated additional second markings 418b may be included, such as markings for a 5 mm surgical tool.

FIG. 5 is a top end view of the device 402 as received within the working chamber 202. As illustrated, the device 402 has six fingers 408, but could alternatively include more or less than six fingers 408, without departing from the scope of the disclosure. In at least one embodiment, for example, the device 402 may employ only three fingers 408. Each finger 408 provides an inner surface 502 configured to engage the outer surface of a surgical tool (not shown)

extended within the cannula 104. In some embodiments, as illustrated, the inner surface 502 may be arcuate (curved) to enable each finger 408 to cradle the outer radial surface of a surgical tool. In other embodiments, however, the inner surface 502 may be flat or of another geometric shape, without departing from the scope of the disclosure.

The fingers 408 extend radially inward toward the centerline B and exhibit an inner diameter 504. As used herein, the inner diameter 504 of the fingers 408 refers to the distance between the terminus of one finger 408 and the terminus of a radially opposite finger 408. In some embodiments, the relaxed inner diameter 504 of the fingers 408 may be the same as or substantially the same as the inner diameter 304 of the cannula 104. In such embodiments, the device 402 may help the cannula 104 center and stabilize a 12 mm surgical tool (e.g., the first surgical tool 306a of FIG. 3), for example. In other embodiments, however, the relaxed inner diameter 504 of the fingers 408 may be smaller than the inner diameter 304 of the cannula 104. In such embodiments, the device 402 may be advantageous in helping center and stabilize smaller surgical tools (e.g., the second surgical tool 306b of FIG. 3) within the cannula 104, such as 8 mm or 5 mm surgical tools.

The inner diameter 504 of the fingers 408 may be adjusted by actuating the device 402, and adjusting the inner diameter 504 may enable the trocar assembly 100 (FIGS. 1-3) to receive, center, and stabilize a variety of surgical tool sizes. As briefly mentioned above, the device 402 may be actuated by rotating the body 404 about the centerline B in either angular direction, as shown by the arrows C and D. Rotating the body 404 in the clockwise direction C, for example, may advance the device 402 deeper into the working chamber 202, while rotating the body 404 in the counter-clockwise direction D may withdraw the device 402 from the working chamber 202. As the device 402 advances into the working chamber 202, the fingers 408 will eventually engage an inner frustoconical surface 506 of the working chamber 202. Engaging the inner frustoconical surface 506 will urge the fingers 408 radially inward toward the centerline B, which simultaneously reduces the magnitude (size) of the inner diameter 504.

The fingers 408 may be flexible to allow the inner diameter 504 to contract (adjust) upon slidably engaging the inner frustoconical surface 506. Once disengaged from the inner frustoconical surface 506, the fingers 408 and the inner diameter 504 will naturally and elastically return to their relaxed and natural state. To provide the required flexibility, the fingers 408 may be made of a resilient material. In some embodiments, the fingers 408 will be made of the same material used to manufacture the seal cartridge 204 (FIG. 2), but this is not required. Suitable flexible materials for the fingers 408 include, but are not limited to, stainless steel, spring steel, plastic, nylon, vinyl, polyurethane, polyethylene, polypropylene, rubber (e.g., natural rubber, synthetic rubber, nitrile rubber, silicone rubber, a urethane rubber, a polyether rubber, chloroprene rubber, ethylene propylene diene monomer, styrene-butadiene rubber, etc.), silicone, or any combination thereof.

FIGS. 6A and 6B are cross-sectional side views of the device 402 during example operation, according to one or more embodiments. As illustrated, the body 404 is received within the working chamber 202 of the housing 102 via the threaded engagement provided by the opposing series of threads 412, 414. Once the device 402 is properly received within the working chamber 202, the centerline A of the cannula 104 may coaxially align with the centerline B of the device 402.

In FIG. 6A, the device 402 is in a first or relaxed configuration. In the relaxed configuration, the fingers 408 are in their relaxed state and naturally extend radially inward toward the centerline B in a generally frustoconical shape. In the illustrated embodiment, the relaxed inner diameter 504 is substantially similar to the inner diameter 304 of the cannula 104. The first surgical tool 306a (depicted in dashed lines) extends through the device 402 and into the cannula 104. Since the outer diameter 308 of the first surgical tool 306a is slightly smaller than the inner diameter 304 of the cannula 104, the first surgical tool 306a may be centered within the lumen 302 using both the cannula 104 and the device 402.

In FIG. 6B, the device 402 has been actuated (rotated) to a second or actuated configuration, thereby altering the inner diameter 504 of the fingers 408. More specifically, the device 402 has been actuated to advance the body 404 into the working chamber 202 until engaging the inner frustoconical surface 506. Continued actuation of the device 402 allows the fingers 408 to slidingly engage the inner frustoconical surface 506, which urges the fingers 408 to radially collapse toward the centerline B and thereby decrease the size of the inner diameter 504. The smaller inner diameter 504 thus becomes the effective inner diameter of the cannula 104. As illustrated, the second surgical tool 306b (depicted in dashed lines) extends through the device 402 and into the cannula 104. The smaller inner diameter 504 operates to center the smaller-diameter second surgical tool 306b within the lumen 302 and thereby eliminate or significantly minimize unwanted occurrences of deflection, oscillation, and vibration of the second surgical tool 306b.

In one or more embodiments, the fingers 408 may be made of or otherwise coated with a lubricious (e.g., slippery or slick) material, thereby reducing the drag force of any surgical tool passing therethrough. In such embodiments, the fingers 408 may be coated with a biocompatible lubricious substance. Suitable lubricious materials include, but are not limited to, oil, graphite, TEFLON™, silicone, parylene, medical fluid, or any combination thereof.

Figure 7B:
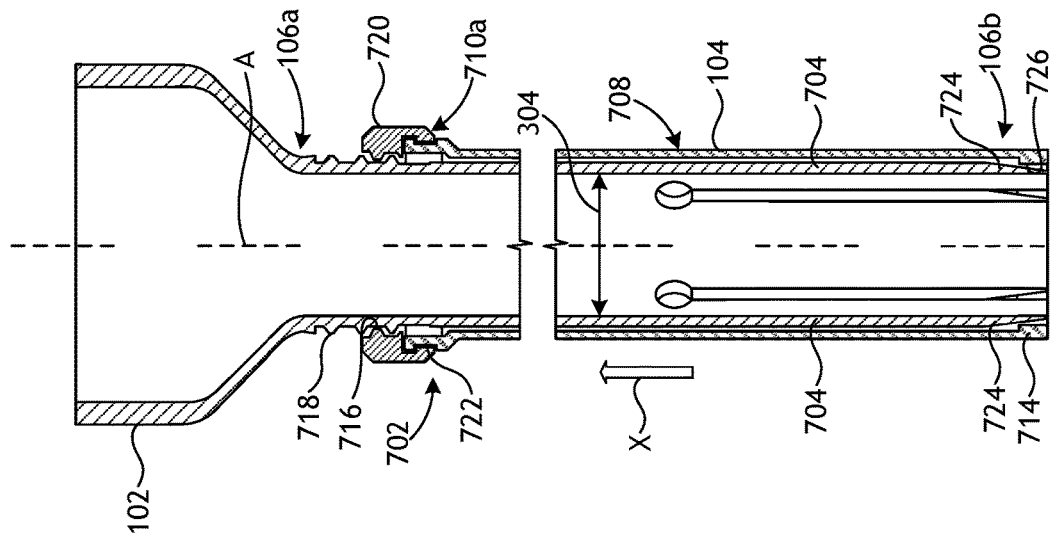
FIG. 7B is a cross-sectional side view of the tool stabilizing device of FIG. 7A in conjunction with the housing and the cannula.
Figure 7A:
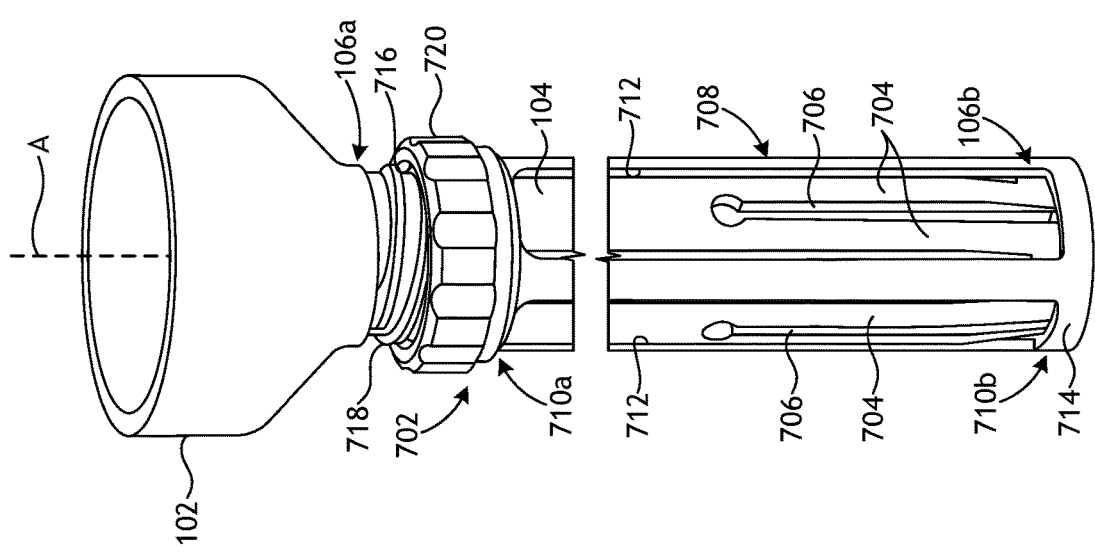
FIG. 7A is an isometric view of another example tool stabilizing device that may be incorporated into the trocar assembly of FIGS. 1-3.

FIG. 7A is an isometric view of another example tool stabilizing device 702 that may be incorporated into the trocar assembly 100 of FIGS. 1-3, according to one or more embodiments. The tool stabilizing device 702 (hereafter "the device 702") may be similar in some respects to the device 402 of FIGS. 4, 5, and 6A-6B and, therefore, may be best understood with reference thereto. Similar to the device 402 of FIGS. 4, 5, and 6A-6B, the device 702 may be actuatable to help center and stabilize surgical tools of varying diameters that may be introduced into the cannula 104.

In the illustrated embodiment, the device 702 may be arranged about the exterior of the cannula 104. In other embodiments, however, the device 702 may alternatively be arranged about the exterior of the housing 102 and the cannula 104, without departing from the scope of the disclosure. As illustrated, the cannula 104 may provide and otherwise define a plurality of longitudinal fingers 704 separated by a corresponding plurality of slots 706. The slots 706 extend to the distal end 106b of the cannula 104, thereby allowing the fingers 704 to freely flex radially inward when the device 702 is actuated.

The device 702 includes a body 708 in the form of a sleeve that may be extended at least partially over the exterior of the cannula 104. The body 708 provides a proximal end 710a and a distal end 710b. In some embodiments, as illustrated, the body 708 may define one or more windows 712 and, in at least one embodiment, one or more of the windows 712 may extend substantially between the proximal and distal ends 710a,b. As will be appreciated, the windows 712 may prove advantageous in reducing tool weight and manufacturing costs. In other embodiments, however, the windows 712 may be omitted and the body 708 may instead provide an unbroken annular structure, without departing from the scope of the disclosure.

A ring 714 may be provided at the distal end 710b of the body 708. In some embodiments, the ring 714 may form an integral part of the body 708, but may alternatively comprise a separate structural element that is coupled to the body 708. When the device 702 is actuated, the ring 714 may be configured to interact with the fingers 704 to adjust the inner diameter 304 (FIG. 3) of the cannula 104.

In some embodiments, the body 708 may be threadably coupled to the cannula 104 at or near the proximal end 106a of the cannula 104. More specifically, the body 708 may provide a series of internal threads 716 (occluded in FIG. 7A) configured to mate with an opposing series of external threads 718 defined on the exterior of the cannula 104 at or near the proximal end 106a. As will be appreciated, design modifications to the body 708 may result in the threads 716 being arranged internally to the body 708 and the threads 718 being arranged externally to the cannula 104, without departing from the scope of the disclosure.

In at least one embodiment, the body 708 may also include a gripping interface 720 at or near the proximal end 710a of the body 708. In some embodiments, the gripping interface 720 may form an integral part of the body 708, but may alternatively comprise a separate structural element that is coupled to the proximal end 710a of the body 708. Similar to the gripping interface 416 of FIG. 4, the gripping interface 720 may provide a location for a user (i.e., a surgeon or clinician) to grasp and actuate the device 702. Depending on the angular direction, rotating (actuating) the device 702 about the centerline A and relative to the cannula 104 and/or housing 102 will advance the body 708 proximally or distally via the threaded interface.

FIG. 7B is a cross-sectional side view of the device 702 in conjunction with the housing 102 and the cannula 104, according to one or more embodiments. In the illustrated embodiment, the gripping interface 720 comprises a separate structural element that may be coupled to the body 708 at an annular groove 722 defined at or near the proximal end 710a of the body 708. In some embodiments, the gripping interface 720 may rotate relative to the body 708. In other embodiments, however, the gripping interface 720 may be attached to the body 708 such that rotation of the gripping interface 720 correspondingly rotates the entire body 708 in the same angular direction. In either embodiment, rotation of the gripping interface 720 about the centerline A causes the body 708 to move proximally or distally (depending on the angular rotational direction) via the threaded engagement.

The fingers 704 may each provide a tapered (angled) outer portion 724 configured to interact with an annular shoulder 726 provided by the ring 714. The annular shoulder 726 extends radially inward to engage the tapered outer portion 724 of each finger 704. In some embodiments, as illustrated, the tapered outer portions 724 (and the ring 714) may be provided at or near the distal end 106b of the cannula 104. In other embodiments, however, the tapered outer portions 724 (and the ring 714) may be provided at any location along the cannula 104, without departing from the scope of the disclosure.

The device 702 may be actuated to adjust the effective inner diameter 304 of the cannula 104 and thereby help center and stabilize surgical tools of varying diameters within the cannula 104. The device 702 may be actuated by rotating the gripping interface 720 relative to the housing 102 and/or the cannula 104. This may result in the body 708 moving proximally or distally (depending on the angular rotational direction) via the threaded interface 716, 718 between the body 708 and the cannula 104. Similar to the device 402 of FIGS. 4, 5, and 6A-6B, the device 702 may be actuated manually or the actuation may be automated. A user (i.e., a surgeon or clinician), for example, may grasp the gripping interface 720 and manually rotate the device 702 to move the body 708 proximally or distally. Alternatively, a motor or a robot that includes an actuation arm may be attached to the device 702 (e.g., at the gripping interface 720) and used to rotate the device 702 and thereby move the body 708 proximally or distally. In yet other embodiments, the device 702 may be actuated through a combination of manual and automated actuation, without departing from the scope of the disclosure.

When the device 702 is actuated to move the body 708 proximally, as shown by the arrow X, the annular shoulder 726 engages the tapered outer portion 724 of each finger 704 and urges the fingers 704 radially inward toward the centerline A. Urging the fingers 704 radially inward simultaneously reduces the magnitude (size) of the inner diameter 304 of the cannula 104 at that location, and reducing the inner diameter 304 may help center and stabilize smaller-diameter surgical tools that may be introduced into the cannula 104.

In some embodiments, the pitch of the opposing threads 716, 718 may be designed such that a predetermined amount of angular rotation will correspondingly change the inner diameter 304 to a predetermined magnitude (e.g., 12 mm, 8 mm, 5 mm, etc.). Moreover, similar to the device 402 of FIG. 4, the device 702 may incorporate markings (not shown) that allow a user to visually track the rotational progress of the device 702 during actuation.

Figure 8A:
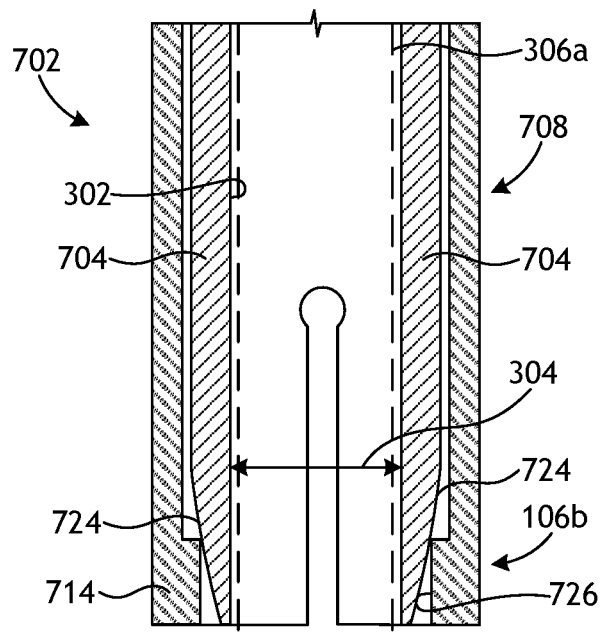
FIGS. 8A and 8B are enlarged cross-sectional views of the distal end of the cannula during example operation of the tool stabilizing device of FIG. 7A.
Figure 8B:
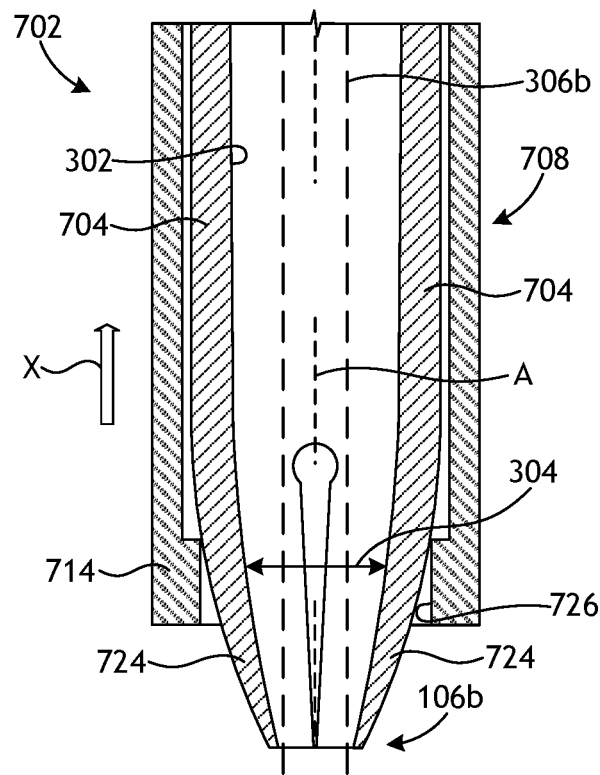

FIGS. 8A and 8B are enlarged cross-sectional views of the distal end 106b of the cannula 104 during example operation of the device 702, according to one or more embodiments. Actuation of the device 702 may be configured to move the body 708 between a first position, as shown in FIG. 8A, and a second position, as shown in FIG. 8B. In FIG. 8A, the fingers 704 at the distal end 106b of the cannula 104 are in a relaxed configuration, thereby exhibiting a natural (full) inner diameter 304 of the cannula 104 at that location. The first surgical tool 306a is depicted in dashed lines as extended into the cannula 104, and the fingers 704 operate to help center the first surgical tool 306a within the lumen 302.

In FIG. 8B, the device 702 has been actuated to the second position, thereby altering the effective inner diameter 304 of the cannula 104 at the location of the fingers 704. More specifically, the device 702 has been actuated by moving the body 708 in the proximal direction X. As the body 708 advances proximally, the annular shoulder 726 provided by the ring 714 will slidingly engage the tapered outer portion 724 of each finger 704 and correspondingly urge the fingers 704 radially inward, which simultaneously reduces the magnitude of the inner diameter 304 of the cannula 104 at the location of the fingers 704. As illustrated, the second surgical tool 306b is depicted in dashed lines as extended through the cannula 104. The smaller inner diameter 304 following actuation of the device 702 operates to center the smaller-diameter second surgical tool 306b within the lumen 302 and thereby eliminate or significantly minimize unwanted occurrences of deflection, oscillation, and vibration of the second surgical tool 306b.

In one or more embodiments, the fingers 704 may be made of or otherwise coated with a lubricious (e.g., slippery or slick) material, thereby reducing the drag force of any surgical tool passing therethrough. In such embodiments, the fingers 704 may be coated with a biocompatible lubricious substance or material such as, but not limited to, oil, graphite, TEFLON™, silicone, parylene, medical fluid, or any combination thereof.

FIG. 9A is an isometric view of another example tool stabilizing device 902 that may be incorporated into the trocar assembly 100 of FIGS. 1-3, according to one or more embodiments. The tool stabilizing device 902 (hereafter "the device 902") may be similar in some respects to the device 702 of FIGS. 7A-7B and 8A-8B and therefore may be best understood with reference thereto, where like numerals will refer to like elements not described again in detail. Similar to the device 702 of FIGS. 7A-7B and 8A-8B, the device 902 may be actuatable to help center and stabilize surgical tools of a variety of sizes within the cannula 104, which again includes the longitudinal fingers 704 separated by the slots 706. Moreover, similar to the device 702 of FIGS. 7A-7B and 8A-8B, the device 902 includes the body 708 having the ring 714 provided at or near the distal end 710b of the body 708, and the gripping interface 720 is provided at or near the proximal end 710a of the body 708.

Unlike the device 702 of FIGS. 7A-7B and 8A-8B, however, the device 902 may be extended at least partially over the exterior of the cannula 104 and the housing 102. As illustrated, the body 708 may provide a cage-like structure 904 that provides a transition between the housing 102 and the cannula 104. The body 708 may be threadably coupled to the housing 102 at a threaded interface comprising the series of internal threads 715 (occluded in FIG. 9A) defined on the body 708, and the opposing series of external threads 716 defined on the housing 102. In the illustrated embodiment, the internal threads 715 are provided on the gripping interface 720, which may be rotated to actuate the device 902. Depending on the angular direction, rotating (actuating) the device 902 about the centerline A and relative to the housing 102 will advance the body 708 proximally or distally via the threaded interface.

FIG. 9B is a cross-sectional side view of the device 902 used in conjunction with the housing 102 and the cannula 104, according to one or more embodiments. In the illustrated embodiment, the gripping interface 720 again comprises a separate structural element that may be coupled to the body 708 at the annular groove 722 defined at or near the proximal end 710a of the body 708. Rotation of the gripping interface 720 causes the body 708 to move proximally or distally (depending on the angular rotational direction) via the threaded engagement 714, 716. As illustrated, the fingers 704 may again each provide tapered (angled) portions 724 configured to interact with the annular shoulder 726 of the ring 714.

Actuation of the device 902 is substantially similar to actuation of the device of FIGS. 7A-7B and 8A-8B and, therefore, will not be described again in detail. When the device 902 is actuated to move the body 708 in the proximal direction X, the annular shoulder 726 will engage the tapered outer portion 724 of each finger 704 and urge the fingers 704 radially inward toward the centerline A, which simultaneously reduces the magnitude of the inner diameter 304 of the cannula 104 at that location. Accordingly, actuating the device 902 may result in adjusting the effective inner diameter 304 of the cannula 104 to help center and stabilize surgical tools of varying diameters within the cannula 104.

FIG. 10A is a cross-sectional side view of a trocar assembly 1000 that incorporates another example tool stabilizing device 1002, according to one or more embodiments. The trocar assembly 1000 may be similar to the trocar assembly 100 of FIGS. 1-3 and, therefore, may be best understood with reference thereto. For example, trocar assembly 1000 includes the housing 102 and the cannula 104 that extends distally from the housing 102. In addition, the tool stabilizing device 1002 (hereafter "the device 1002") may be similar in some respects to the devices 402, 702, and 902 described herein and, therefore, may be best understood with reference thereto. For instance, similar to the devices 402, 702, and 902, the device 1002 may help center and stabilize surgical tools of varying diameters that may be introduced into the cannula 104.

In the illustrated embodiment, the device 1002 is received and seated within the working chamber 202 of the housing 102. The seal cartridge 204 is also shown as received within the working chamber 202, and the device 1002 may be arranged below or distal to the seal cartridge 204. The seal assemblies 204a,b (FIG. 2) are not shown in FIG. 9A. In at least one embodiment, the device 1002 may be seated within an annular groove 1004 defined by the housing 102 within the working chamber 202. As will be appreciated, however, the device 1002 may be positioned or received within the working chamber 202 via any suitable means, such as using mechanical fasteners, an interference fit, etc.

FIG. 10B is a partial exploded view of the trocar assembly 1000 of FIG. 10A. As illustrated, the seal cartridge 204 is suspended outside of the working chamber 202 and the device 1002 is received within the working chamber 202 at the annular groove 1004. The device 1002 may provide a generally annular body 1006 and a plurality of radial adjustment leaves 1008 extending radially inward from the annular body 1006. Each radial adjustment leaf 1008 may be coupled to the body 1006 by a corresponding stem 1010 that extends between the annular body 1006 and the associated radial adjustment leaf 1008. While four radial adjustment leaves 1008 are shown in FIG. 10B, more or less than four radial adjustment leaves 1008 may be employed, without departing from the scope of the disclosure. In at least one embodiment, for example, it is contemplated herein to employ only three radial adjustment leaves 1008.

The radial adjustment leaves 1008 cooperatively form an iris 1012 at the center of the device 1002, and the iris 1012 has a diameter 1014 that may be adjusted to accommodate surgical tools of varying sizes. In the illustrated embodiment, the diameter 1014 is in a relaxed or natural state. During operation of the trocar assembly 1000, however, surgical tools of a variety of sizes may be passed through the iris 1012 and into the cannula 104. When a surgical tool having an outer diameter substantially similar to the natural diameter 1014 of the iris 1012 is introduced into the trocar assembly 100, the leaves 1008 help support and center the surgical tool within the trocar assembly 100 (e.g., the cannula 104). In contrast, when a surgical tool having an outer diameter larger than the natural diameter 1014 of the iris 1012 is introduced into the trocar assembly 100, the magnitude of the diameter 1014 may increase as the leaves 1008 flex radially outward via the corresponding stems 1010 to accommodate the larger surgical tool. Accordingly, the device 1002 may prove advantageous in dynamically (compliantly) receiving, centering, and stabilizing surgical tools of varying sizes within the cannula 104.

Figure 11A:
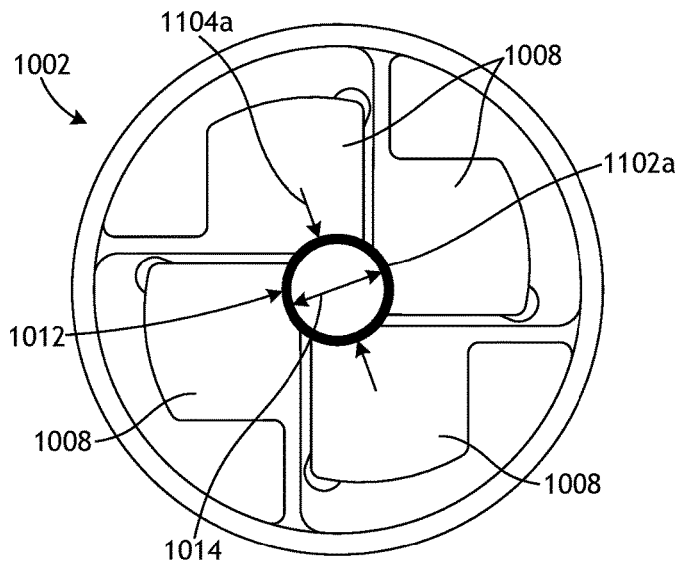
FIGS. 11A-11C are progressive top views of the tool stabilizing device of FIGS. 10A-10B showing example operation.
Figure 11B:
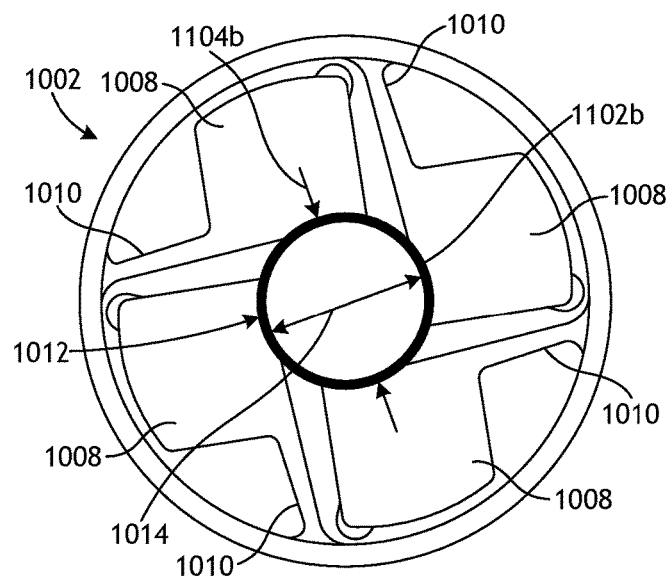
Figure 11C:
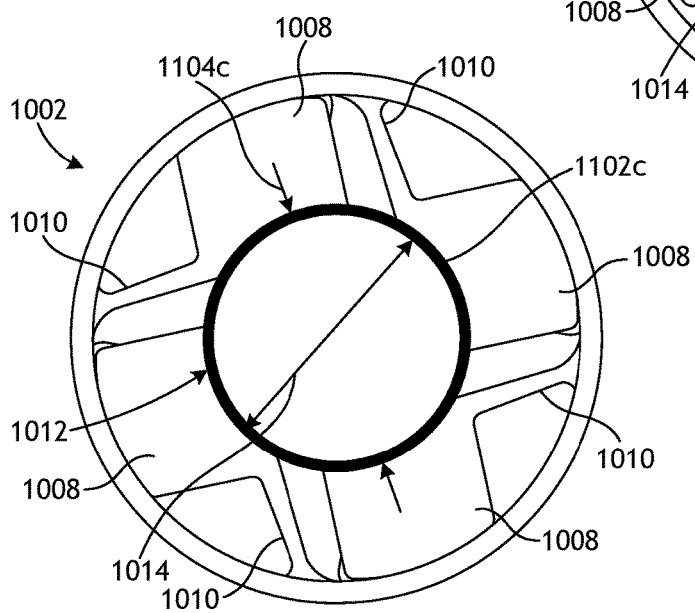

FIGS. 11A-11C are progressive top views of the device 1002 showing example operation of the device 1002. In FIG. 11A, a first surgical tool 1102a having a first outer diameter 1104a is shown extended axially through the iris 1012 of the device 1002. The first outer diameter 1104a may be substantially similar to or slightly smaller than the diameter 1014 of the iris 1012. In at least one embodiment, for example, the first outer diameter 1104a may be approximately 5 mm and the first surgical tool 1102a may, therefore, be characterized as a 5 mm surgical tool. As the first surgical tool 1102a extends through the iris 1012, the leaves 1008 may engage or come into close contact with the outer surface of the first surgical tool 1102a, but the diameter 1014 may remain substantially in its relaxed or natural state. Nonetheless, the leaves 1008 may still help to center and stabilize the first surgical tool 1102a within the underlying cannula 104 (FIGS. 10A-10B).

In FIG. 11B, a second surgical tool 1102b having a second outer diameter 1104b is shown extended through the iris 1012 of the device 1002. The second outer diameter 1104b may be larger than the first outer diameter 1104a (FIG. 11A) and larger than the relaxed or natural diameter 1014 of the iris 1012. In at least one embodiment, for example, the second outer diameter 1104b may be approximately 8 mm and the second surgical tool 1102b may, therefore, be characterized as an 8 mm surgical tool. As the second surgical tool 1102b extends through the iris 1012, the leaves 1008 engage the outer surface of the second surgical tool 1102b and the diameter 1014 of the iris increases as the leaves 1008 are urged radially outward to accommodate the larger second surgical tool 1102b. The stem of 1010 of each leaf 1008 may be flexible to allow the leaves 1008 to move radially outward, but also provide a compliant biasing force that helps the leaves 1008 center and stabilize the second surgical tool 1102b within the underlying cannula 104 (FIGS. 10A-10B).

In FIG. 11C, a third surgical tool 1102c having a third outer diameter 1104c is shown extended through the iris 1012 of the device 1002. The third outer diameter 1104c may be larger than the second outer diameter 1104b (FIG. 11B). In at least one embodiment, for example, the third outer diameter 1104c may be approximately 12 mm and the third surgical tool 1102c may, therefore, be characterized as a 12 mm surgical tool. As the third surgical tool 1102c extends through the iris 1012, the leaves 1008 engage the outer surface of the third surgical tool 1102b and the diameter 1014 of the iris increases as the leaves 1008 are urged radially outward to accommodate the larger third surgical tool 1102b. The flexible stem of 1010 of each leaf 1008 allow the leaves 1008 to move radially outward, but also provide a compliant biasing force that helps the leaves 1008 center and stabilize the third surgical tool 1102c within the underlying cannula 104 (FIGS. 10A-10B).

Figures 12A, 12B:
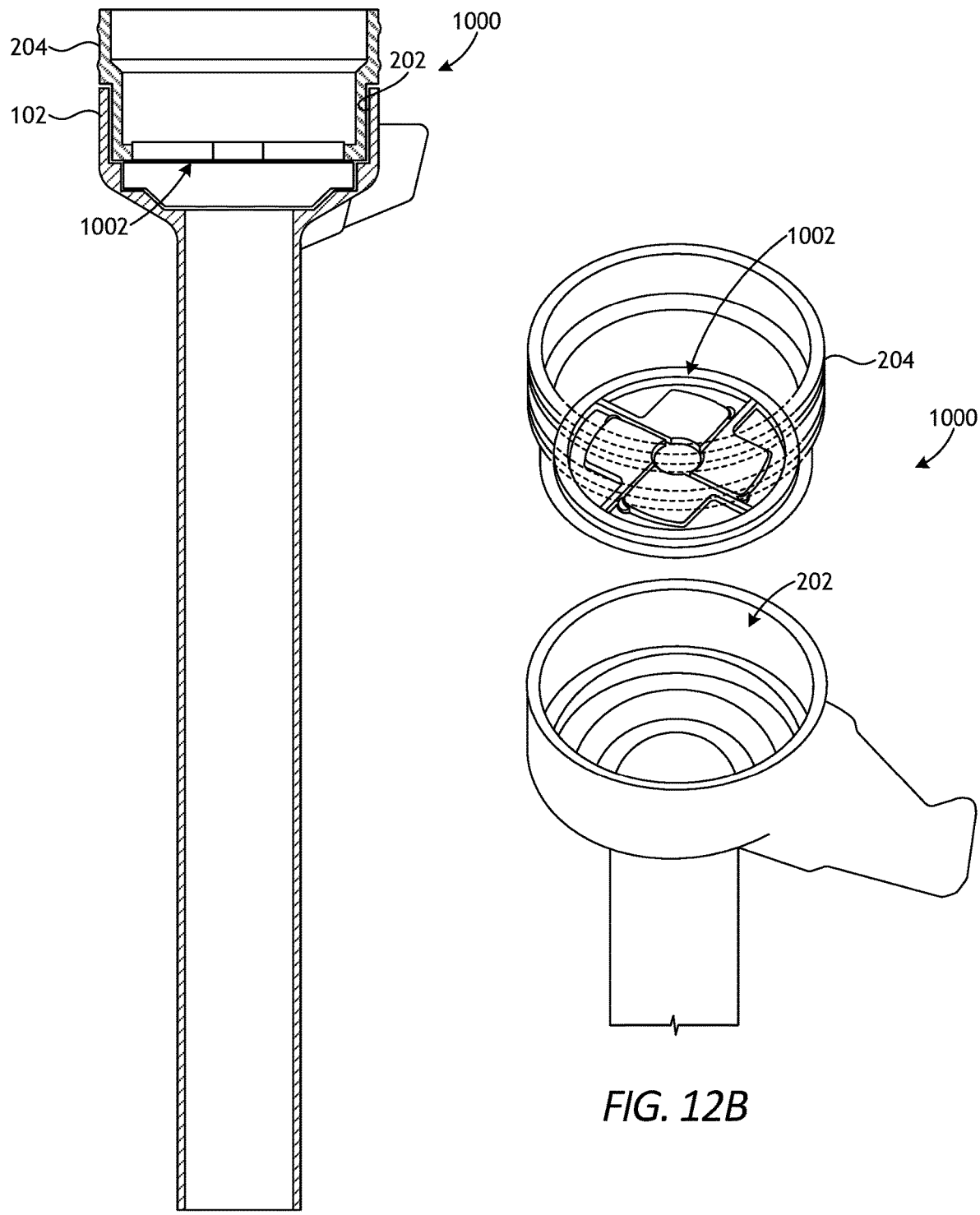
FIG. 12A is a cross-sectional view of the trocar assembly of FIG. 10A showing an alternative embodiment of the tool stabilizing device of FIGS. 10A-10B.
FIG. 12B is a partial exploded view of the trocar assembly of FIG. 12A.

FIG. 12A is a cross-sectional view of the trocar assembly 1000 incorporating an alternative embodiment of the device 1002 of FIGS. 10A-10B. In the illustrated embodiment, the device 1002 is again received and seated within the working chamber 202 of the housing 102. However, unlike the embodiment of FIGS. 10A-10B, the device 1002 may alternatively be positioned within the seal cartridge 204. In some embodiments, the device 1002 may form an integral part of the seal cartridge 204. In other embodiments, however, the device 1002 may comprise an independent structure received by and otherwise seated within the seal cartridge 204. While not shown, in at least one embodiment, the device 1002 may be positioned proximal to the seal assemblies 204a,b (FIG. 2), without departing from the scope of the disclosure.

FIG. 12B is a partial exploded view of the trocar assembly 1000 of FIG. 12A. As illustrated, the seal cartridge 204 is suspended outside of the working chamber 202 and the device 1002 is received within the seal cartridge 204.

Operation of the device 1002 shown in FIGS. 12A and 12B is substantially similar to operation of the device 1002 shown in FIGS. 11A-11C and, therefore, will not be described again in detail.

Figure 13A:
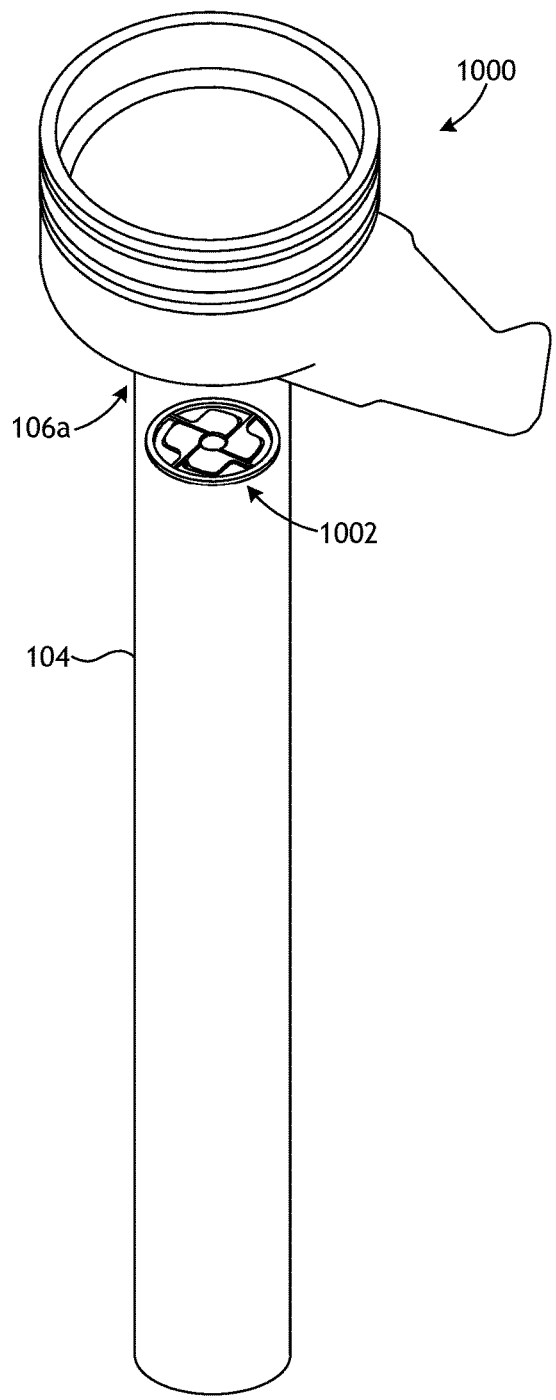
FIGS. 13A and 13B depict alternative placement of the tool stabilizing device of FIGS. 10A-10B.
Figure 13B:
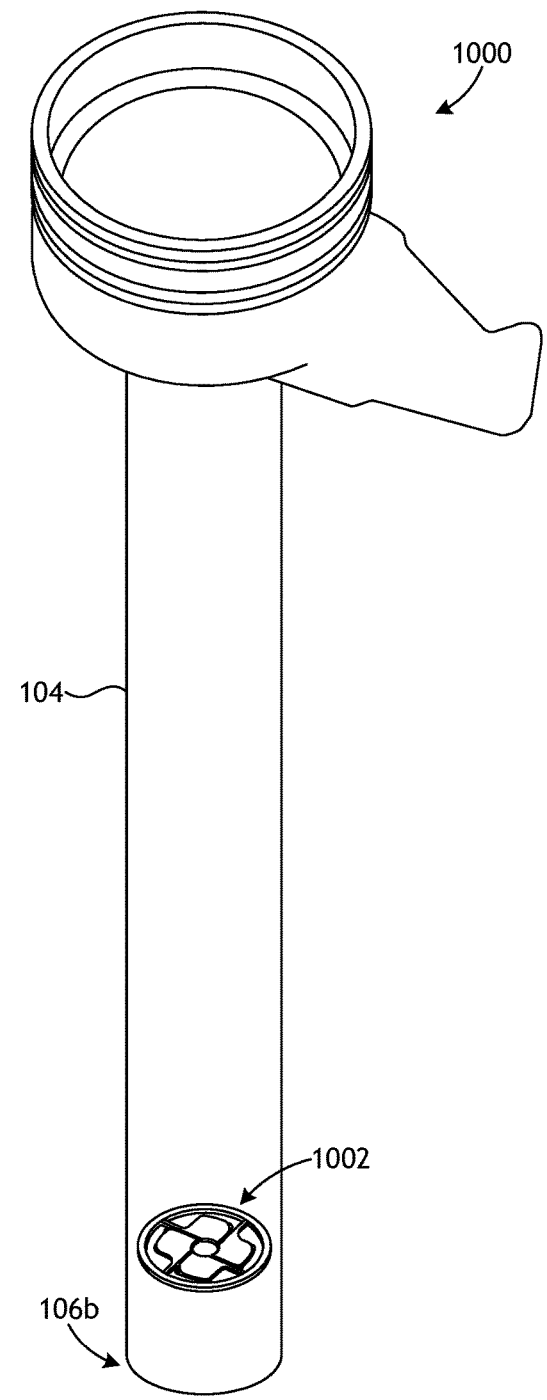

FIGS. 13A and 13B depict alternative placement of the device 1002 of FIGS. 10A-10B on the trocar assembly 1000, according to one or more embodiments. The device 1002 may be positioned at a variety of locations in the trocar assembly 1000 and still function to center and stabilize surgical tools of varying diameters within the cannula 104. In FIG. 13A, for example, the device 1002 may be positioned at or near the proximal end 106a of the cannula 104. In FIG. 13B, the device 1002 may be positioned at or near the distal end 106b of the cannula 104. In yet other embodiments, the device 1002 may be positioned at a location intermediate to the first and second ends 106a,b, without departing from the scope of the disclosure. As will be appreciated, the position of the device 1002 is not limited to any location in the trocar assembly 1000. The device 1002 may be secured in such locations by, for example, an interference fit, mechanical fasteners, snapping into a groove, welding, or with an industrial adhesive.

FIG. 14 is an isometric view of another trocar assembly 1400 that incorporates another example tool stabilizing device 1402, according to one or more embodiments. The trocar assembly 1400 may be similar to the trocar assembly 100 of FIGS. 1-3 and, therefore, may be best understood with reference thereto. For example, trocar assembly 1400 includes the housing 102 and the cannula 104 that extends distally from the housing 102. In addition, the tool stabilizing device 1402 (hereafter "the device 1402") may be similar in some respects to the devices 402, 702, 902, and 1002 described herein and, therefore, may be best understood with reference thereto. For instance, similar to the devices 402, 702, 902, and 1002, the device 1402 may be actuated to help center and stabilize surgical tools of varying diameters that may be introduced into the cannula 104.

In the illustrated embodiment, the device 1402 may be arranged within the working chamber 202. In some embodiments, the device 1402 may form an integral part of the housing 102, such as providing a portion of the outer wall of the housing 102. In other embodiments, however, the device 1402 may comprise a separate structural element merely received within the working chamber 202. In yet other embodiments, the device 1402 may be arranged in other locations within the trocar assembly 1400. For example, the device 1402 may alternatively be positioned at any location along the cannula 104, without departing from the scope of the disclosure.

FIGS. 15A and 15B are isometric top and bottom views, respectively, of an example embodiment of the device 1402. As illustrated, the device 1402 may include a cam plate 1502, a lug plate 1504, and a plurality of lugs 1506. The device 1402 has a centerline B configured to align coaxially with the centerline A (FIG. 14) of the trocar assembly 1400 (FIG. 14) when the device 1402 is properly positioned therein. The lugs 1506 cooperatively define an iris 1508, and the centerline B passes through (or near) the center of the iris 1508. The cam and lug plates 1502, 1504 may be configured to move relative to one another to cooperatively move the lugs 1506 radially inward and outward relative to the centerline B and thereby adjust the size (diameter) of the iris 1508.

As best seen in FIG. 15A, the cam plate 1502 defines a central aperture 1509 that provides a cam profile 1510, and, as best seen in FIG. 15B, the lug plate 1504 provides and otherwise defines a plurality of slots 1512. The slots 1512 extend radially outward from the centerline B and are interconnected (contiguous) at the center of the lug plate 1504 (i.e., at the location of the iris 1508). One lug 1506 is received into each slot 1512, and each lug 1506 has a depth (or height) large enough to interact with both the cam profile 1510 and the slots 1512 during operation.

While three lugs 1506 and three corresponding slots 1512 are depicted in FIGS. 15A and 15B, more or less than three lugs 1506 and corresponding slots 1512 may be employed in the device 1402, without departing from the scope of the disclosure. Moreover, while the slots 1512 are depicted as being equidistantly spaced from each other by about 120°, the slots 1512 may alternatively be non-equidistantly spaced from each other, without departing from the scope of the disclosure.

In some embodiments, as best seen in FIG. 15B, each lug 1506 may be biased radially outward (away from the centerline B) with a corresponding biasing device 1514. Each biasing device 1514 may be coupled to an associated lug 1506 and an end wall of a corresponding slot 1512. In the illustrated embodiment, the biasing devices 1514 are depicted as coil springs, but could alternatively comprise any other type of biasing means, such as hydraulic or pneumatic cylinders.

In example operation, one or both of the cam and lug plates 1502, 1504 may be configured to move (rotate) relative to the other about the centerline B. As the cam plate 1502 rotates relative to the lug plate 1504, for example, the lugs 1506 will slidingly engage the cam profile 1510. Moreover, since the lugs 1506 are biased radially outward with the biasing devices 1514, the lugs 1506 will tend to follow the cam profile 1510 as the cam plate 1502 rotates. The biasing devices 1514 may expand and contract to accommodate the undulating curves of the cam profile 1510, and the lugs 1506 will correspondingly translate radially inward and outward relative to the centerline B in response to the cam profile 1510. As the lugs 1506 translate radially relative to the centerline B, the size (diameter) of the iris 1508 will correspondingly change (i.e., increase or decrease). It is noted that, although the example embodiment contains two dwell zones that may accommodate two distinct tool diameters, the cam profile 1510 may alternatively be designed for a continuous adjustment profile that includes a multitude of dwell zones for several distinct tool diameters, without departing from the scope of the disclosure.

Figure 16A:
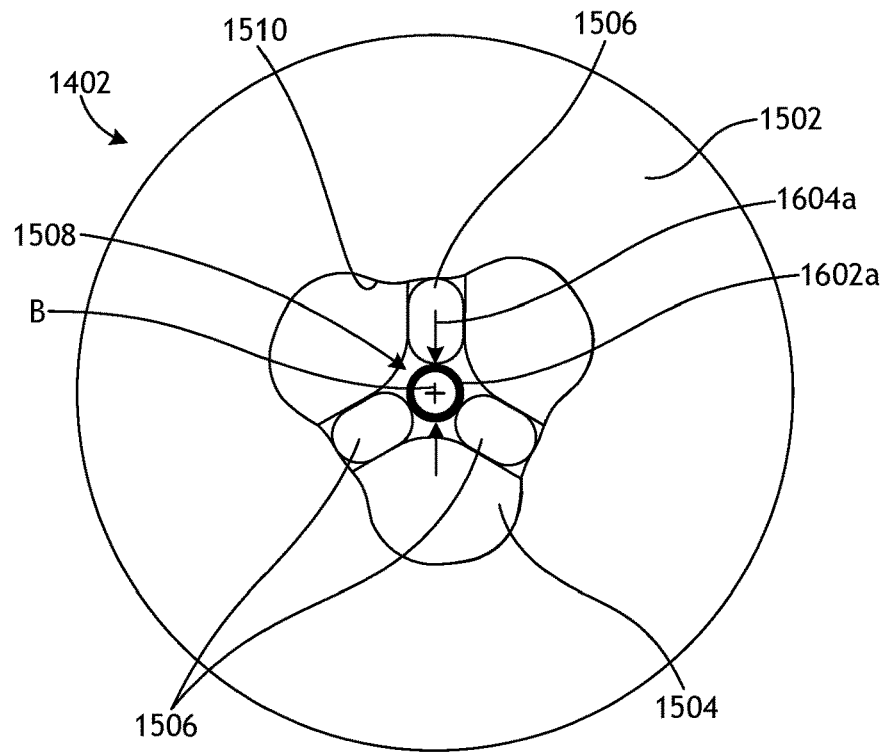
FIGS. 16A and 16B are top views of the tool stabilizing device of FIG. 14 showing example operation.
Figure 16B:
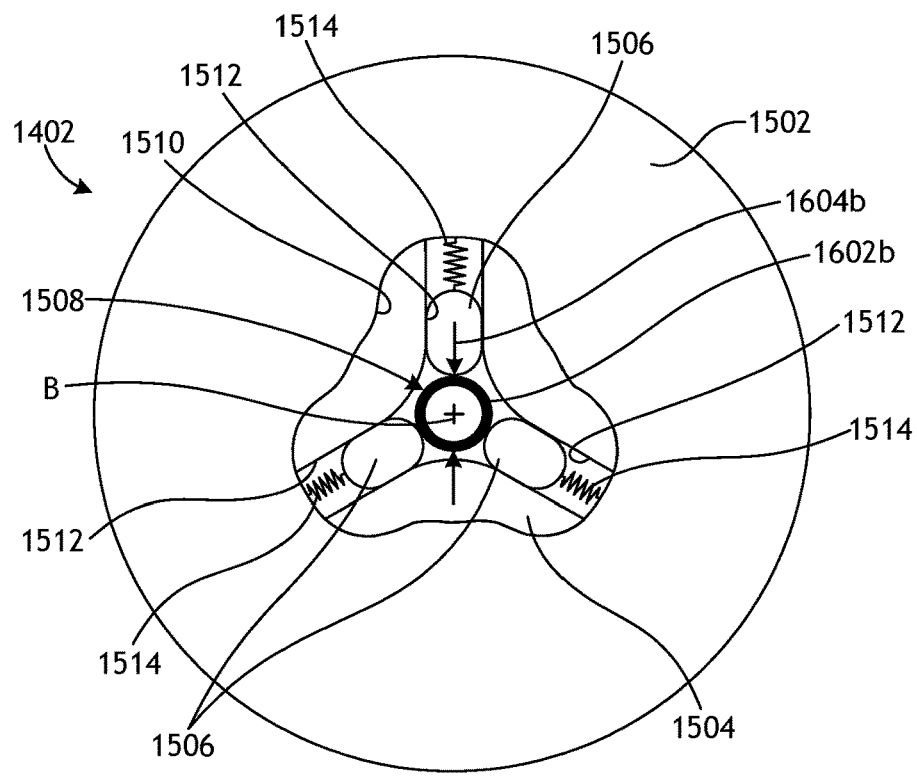

FIGS. 16A and 16B are progressive top views of the device 1402 showing example operation. In FIG. 16A, the cam plate 1502 is positioned relative to the lug plate 1504 such that concave (inwardly extending toward centerline B) lobes of the cam profile 1510 engage each lugs 1506 and urge each lug toward the centerline B. A first surgical tool 1602a having a first outer diameter 1604a is shown extended axially through the iris 1508 of the device 1402. In at least one embodiment, for example, the first outer diameter 1604a may be approximately 5 mm and the first surgical tool 1602a may, therefore, be characterized as a 5 mm surgical tool. As the first surgical tool 1602a extends through the iris 1508, the lugs 1506 may engage or come into close contact with the outer surface of the first surgical tool 1602a and help to center and stabilize the first surgical tool 1602a within the underlying cannula 104 (FIG. 14).

In FIG. 16B, the cam plate 1502 has been actuated (moved) relative to the lug plate 1504 and the cam profile 1510 has correspondingly moved such that the concave (inwardly extending away from centerline B) lobes of the cam profile 1510 no longer engage the lugs 1506. Rather, the lugs 1506 are positioned adjacent corresponding convex (outwardly extending) lobes of the cam profile 1510, which allow the biasing devices 1514 to urge the associated lug 1506 radially outward with respect to the centerline B within the corresponding slot 1512 of the lug plate 1504. Pulling the lugs 1506 radially outward correspondingly increases the size (diameter) of the iris 1508, which allows the device 1402 to accommodate surgical tools of a larger diameter.

A second surgical tool 1602b having a second outer diameter 1604b is shown extended through the enlarged iris 1508 of the device 1402. The second outer diameter 1604b may be larger than the first outer diameter 1604a (FIG. 16A). In at least one embodiment, for example, the second outer diameter 1604b may be approximately 8 mm and the second surgical tool 1602b may, therefore, be characterized as an 8 mm surgical tool. As the second surgical tool 1602b extends through the iris 1508, the lugs 1506 engage the outer surface of the second surgical tool 1602b and help center and stabilize the second surgical tool 1602b within the underlying cannula 104 (FIG. 14).

As will be appreciated, while the above example describes the cam plate 1502 actuating (moving, rotating, etc.) with respect to the lug plate 1504, the lug plate 1504 may alternatively actuate (move, rotate, etc.) with respect to the cam plate 1502 and achieve the same result, without departing from the scope of the disclosure. In yet other embodiments, both of the cam and lug plates 1502, 1504 may be configured to actuate (move, rotate, etc.) relative to the other and achieve the same functional result.

FIG. 17 is an isometric view of another trocar assembly 1700 that incorporates another example tool stabilizing device 1702, according to one or more embodiments. The trocar assembly 1700 may be similar to the trocar assembly 100 of FIGS. 1-3 and, therefore, may be best understood with reference thereto. For example, trocar assembly 1700 includes the housing 102 and the cannula 104 that extends distally from the housing 102. In addition, the tool stabilizing device 1702 (hereafter "the device 1702") may be similar in some respects to the devices 402, 702, 902, 1002, and 1402 described herein and, therefore, may be best understood with reference thereto. For instance, similar to the devices 402, 702, 902, 1002, and 1402, the device 1702 may be actuated to help center and stabilize surgical tools of varying diameters that may be introduced into the cannula 104.

In the illustrated embodiment, the device 1702 may be arranged within the working chamber 202. In some embodiments, the device 1702 may form an integral part of the housing 102, such as providing a portion of the outer wall of the housing 102. In other embodiments, however, the device 1702 may comprise a separate structural element merely received within the working chamber 202. In yet other embodiments, the device 1702 may be arranged in other locations within the trocar assembly 1700. For example, the device 1702 may alternatively be positioned at any location along the cannula 104, without departing from the scope of the disclosure.

FIGS. 18A and 18B are isometric top and bottom views, respectively, of an example embodiment of the device 1702. As illustrated, the device 1702 may include an outer ring 1802 and an inner ring 1804 concentrically located within the outer ring 1802. The inner ring 1804 is received within and otherwise coaxial with the outer ring 1802. Moreover, the inner ring 1804 defines a central aperture 1806 configured to receive surgical tools passing through the device 1702 and into the cannula 104 (FIG. 17). The device 1702 has a centerline B that extends through the central aperture 1806 and aligns coaxially with the centerline A (FIG. 17) of the trocar assembly 1700 (FIG. 17) when the device 1702 is properly positioned therein.

The inner and outer rings 1802, 1804 are configured to rotate relative to one another about the centerline B. In some embodiments, the outer ring 1802 may be actuated to rotate relative to the inner ring 1804. In other embodiments, however, the inner ring 1804 may be actuated to rotate relative to the outer ring 1802. In yet other embodiments, both the inner and outer rings 1802, 1804 may be actuated simultaneously (albeit in opposite angular directions) to rotate relative to the other, without departing from the scope of the disclosure.

The device 1702 may further include a plurality of mechanical linkages 1808. Each mechanical linkage 1808 may include a first link 1810a operatively coupled to the outer ring 1802 at a first pin 1812a, and a second link 1810b operatively coupled to the inner ring 1804 at a second pin 1812b. The first and second links 1810a,b of each mechanical linkage 1808 may then be coupled to each other at a third pin 1812c. The pins 1812a-c allow the links 1810a,b to rotate freely relative to one another and relative to the corresponding outer and inner rings 1802, 1804.

While three mechanical linkages 1808 are depicted in FIGS. 18A and 18B, more or less than three mechanical linkages 1808 may be employed in the device 1702, without departing from the scope of the disclosure. The mechanical linkages 1808, and more particularly the second links 1810b, cooperatively define an iris 1814, and the centerline B passes through the center of the iris 1814. The device 1702 may be actuated to move the outer and inner rings 1802, 1804 relative to one another, which moves the mechanical linkages 1808 and thereby adjusts the size (diameter) of the iris 1814.

In example operation, one or both of the outer and inner rings 1802, 1804 may be configured to move (rotate) relative to the other about the centerline B. As the outer ring 1802 rotates relative to the inner ring 1804, for example, the first link 1810a will cause the second link 1810b to rotate toward the centerline B as pinned at the pins 1812a-c. Moving the second links 1810b toward the centerline B may partially occlude the central aperture 1806 and alter (i.e., decrease) the size (diameter) of the iris 1814. Moving the outer ring 1802 in the opposite direction relative to the inner ring 1804 may cause the second link 1810b to rotate away from the centerline B, and thereby increase the size (diameter) of the iris 1814.

Figure 19A:
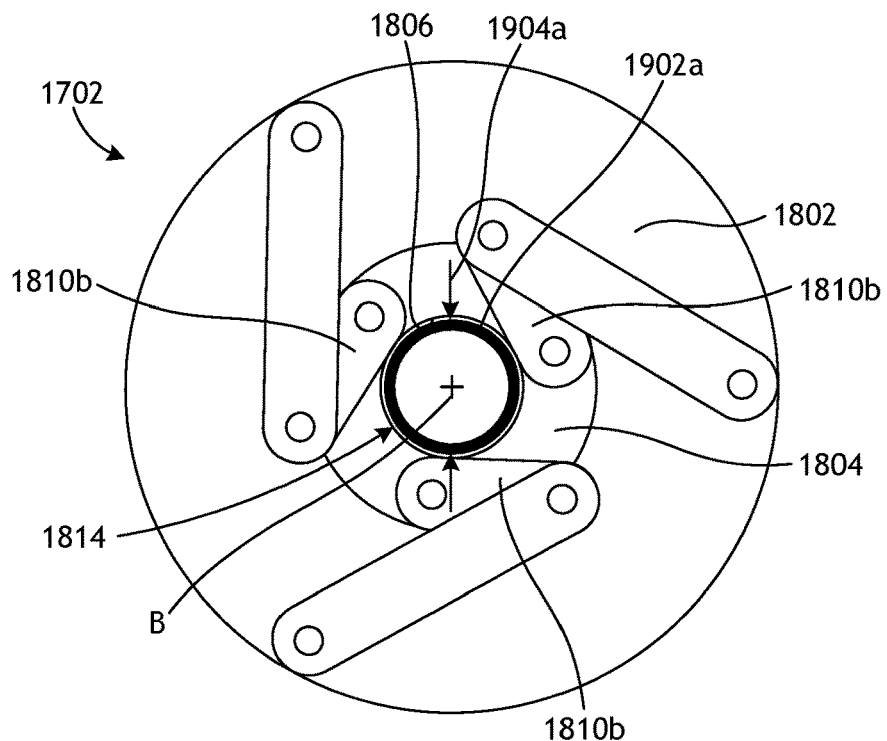
FIGS. 19A and 19B are top views of the tool stabilizing device of FIG. 17 showing example operation.
Figure 19B:
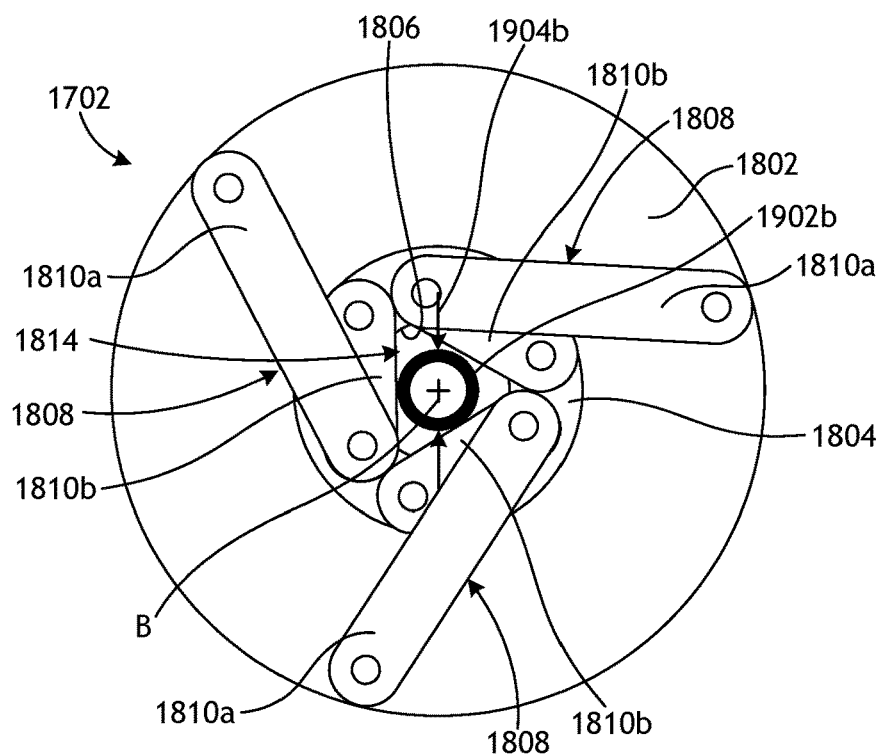

FIGS. 19A and 19B are progressive top views of the device 1702 showing example operation. In FIG. 19A, the outer ring 1802 is positioned relative to the inner ring 1804 such that the iris 1814 defined by the second links 1810b has a diameter that is the same as or larger than the diameter of the central aperture 1806. A first surgical tool 1902a having a first outer diameter 1904a is shown extended axially through the iris 1814 of the device 1702. In at least one embodiment, for example, the first outer diameter 1904a may be approximately 12 mm and the first surgical tool 1902a may, therefore, be characterized as a 12 mm surgical tool. As the first surgical tool 1902a extends through the iris 1814, the mechanical linkages 1808 (e.g., the second links 1810b) may engage or come into close contact with the outer surface of the first surgical tool 1902a and help to center and stabilize the first surgical tool 1902a within the underlying cannula 104 (FIG. 17).

In FIG. 19B, the outer ring 1802 has been actuated (moved) relative to the inner ring 1804 and thereby correspondingly altering the position or orientation of the linkages 1808. More specifically, as the outer ring 1802 rotates relative to the inner ring 1804, the first link 1810a urges the second link 1810b to rotate toward the centerline B, which decreases the size (diameter) of the iris 1814. As illustrated, this may result in the second links 1810b partially occluding the central aperture 1806. A second surgical tool 1902b having a second outer diameter 1904b is shown extended through the enlarged iris 1814 of the device 1702. The second outer diameter 1904b may be smaller than the first outer diameter 1904a (FIG. 19A). In at least one embodiment, for example, the second outer diameter 1904b may be approximately 8 mm and the second surgical tool 1902b may, therefore, be characterized as an 8 mm surgical tool. As the second surgical tool 1902b extends through the iris 1814, the mechanical linkages 1808 (e.g., the second links 1810b) engage the outer surface of the second surgical tool 1902b and help center and stabilize the second surgical tool 1902b within the underlying cannula 104 (FIG. 17).

As will be appreciated, while the above example describes the outer ring 1802 actuating (moving, rotating, etc.) with respect to the inner ring 1804, the inner ring 1804 may alternatively actuate (move, rotate, etc.) with respect to the outer ring 1802 and achieve the same result, without departing from the scope of the disclosure. In yet other embodiments, both of the outer and inner rings 1802, 1804 may be configured to actuate (move, rotate, etc.) relative to the other and achieve the same functional result. Moreover, while the example embodiment of FIGS. 19A and 19B depicts a continuous adjustment mechanism, discrete positions could be provided through the use of a detent, a visual indicator, or another alignment mechanism (similar to other previously described methods), without departing from the scope of the disclosure.

Embodiments disclosed herein include:

A. A trocar assembly that includes a trocar housing that defines a working chamber, a cannula coupled to the trocar housing at a proximal end to facilitate communication between the cannula and the working chamber, and a tool stabilizing device coupled to at least one of the trocar housing and the cannula and actuatable by rotation to stabilize and center a surgical tool within the cannula.

B. A method of using a trocar assembly that includes introducing a surgical tool into a working chamber defined by a trocar housing, wherein the working chamber communicates with a cannula coupled to the trocar housing, and wherein a tool stabilizing device is coupled to at least one of the trocar housing and the cannula, extending the surgical tool into the cannula, and actuating the tool stabilizing device by rotation to stabilize and center the surgical tool within the cannula.

Each of embodiments A and B may have one or more of the following additional elements in any combination: Element 1: wherein the tool stabilizing device comprises an annular body configured to be received within the working chamber, and a plurality of fingers extending from the body and radially inward toward a centerline of the body, the plurality of fingers defining an inner diameter that is adjustable upon actuation of the tool stabilizing device. Element 2: wherein the trocar housing defines a frustoconical inner surface within the working chamber, the frustoconical inner surface being engageable with the plurality of fingers to adjust the inner diameter upon actuation of the tool stabilizing device. Element 3: wherein a diameter of the surgical tool is smaller than an inner diameter of the cannula, and wherein the inner diameter of the plurality of fingers is adjustable to support and center the surgical tool within the cannula. Element 4: wherein the body is coupled to the trocar housing at a threaded interface, and the tool stabilizing device is actuated by rotating the body relative to the trocar housing via the threaded interface. Element 5: wherein a pitch of the threaded interface corresponds to a predetermined amount of rotation of the body to adjust the inner diameter to a predetermined magnitude. Element 6: wherein the tool stabilizing device further comprises a gripping interface that provides a location to engage and rotate the body relative to the trocar housing. Element 7: further comprising a lubricious material coated on the plurality of fingers to mitigate drag against an outer surface of the surgical tool. Element 8: wherein the cannula defines a plurality of fingers and each finger provides a tapered outer portion, and wherein the tool stabilizing device comprises a body arranged about an exterior of one or both of the trocar housing and the cannula, and a ring arranged at a distal end of the body and having an annular shoulder engageable with the tapered outer portion of each finger to adjust an inner diameter of the cannula when the tool stabilizing device is actuated. Element 9: wherein the body is coupled to the exterior of the trocar housing or to the cannula at a threaded interface, and the tool stabilizing device is actuated by rotating at least a portion of the body relative to the trocar housing or the cannula via the threaded interface and thereby moving the ring relative to the tapered outer portion of each finger. Element 10: wherein a pitch of the threaded interface corresponds to a predetermined amount of rotation of the portion of the body to adjust the inner diameter to a predetermined magnitude. Element 11: wherein the portion of the body comprises a gripping interface coupled to the body at an annular groove. Element 12: wherein the annular shoulder biases the fingers radially inward to reduce the inner diameter of the cannula when the tool stabilizing device is actuated.

Element 13: wherein the tool stabilizing device includes an annular body received within the working chamber, and a plurality of fingers extending from the body and radially inward toward a centerline of the body to define an inner diameter, the method further comprising extending the surgical tool through the plurality of fingers, and adjusting the inner diameter of the plurality of fingers upon actuating the tool stabilizing device and thereby stabilizing and centering the surgical tool within the cannula. Element 14: wherein the trocar housing defines a frustoconical inner surface within the working chamber, and wherein adjusting the inner diameter of the plurality of fingers comprises engaging the plurality of fingers against the frustoconical inner surface, and radially collapsing the plurality of fingers to decrease the inner diameter of the plurality of fingers. Element 15: wherein the body is coupled to the trocar housing at a threaded interface and actuating the tool stabilizing device comprises rotating the body relative to the trocar housing via the threaded interface. Element 16: wherein the tool stabilizing device further comprises a gripping interface and actuating the tool stabilizing device further comprises engaging the gripping interface, and rotating the body relative to the trocar housing at the gripping interface. Element 17: wherein the cannula defines a plurality of fingers and each finger provides a tapered outer portion, wherein the tool stabilizing device includes a body arranged about an exterior of one or both of the trocar housing and the cannula, and a ring arranged at a distal end of the body, and wherein actuating the tool stabilizing device comprises engaging an annular shoulder defined by the ring against the tapered outer portion of each finger, and adjusting an inner diameter of the cannula as the annular shoulder engages the tapered outer portion of each finger. Element 18: wherein the body is coupled to the exterior of the trocar housing or the cannula at a threaded interface, and wherein actuating the tool stabilizing device further comprises rotating at least a portion of the body relative to the trocar housing or the cannula via the threaded interface, moving the ring relative to the tapered outer portion of each finger, and biasing the fingers radially inward with the annular shoulder and thereby reducing the inner diameter of the cannula.

By way of non-limiting example, exemplary combinations applicable to A and B include: Element 1 and Element 2; Element 1 and Element 3; Element 1 and Element 4; Element 4 and Element 5; Element 4 and Element 6; Element 1 and Element 7; Element 8 and Element 9; Element 9 and Element 10; Element 9 and Element 11; Element 8 and Element 12; Element 13 and Element 14; Element 13 and Element 15; Element 15 and Element 16; and Element 17 and Element 18.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

The terms "proximal" and "distal" are defined herein relative to a surgeon or robotic surgical system having an interface configured to mechanically and electrically couple a surgical tool to a robotic manipulator. The term "proximal" refers to the position of an element closer to the surgeon or the robotic manipulator and the term "distal" refers to the position of an element further away from the surgeon or the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A trocar assembly, comprising:
 a trocar housing that defines a working chamber;
 a cannula coupled to the trocar housing at a proximal end to facilitate communication between the cannula and the working chamber; and
 a tool stabilizing device including an annular body receivable within the working chamber and a plurality of fingers extending distally from the body and radially inward toward a centerline of the body when the plurality of fingers are in a relaxed state,
 wherein the body is rotatable relative to the trocar housing to engage the plurality of fingers against an inner surface of the working chamber and thereby flex the plurality of fingers radially inward from the relaxed state to stabilize and center a surgical tool within the cannula, and
 wherein disengaging the plurality of fingers from the inner surface allows the plurality of fingers to elastically return to the relaxed state.

2. The trocar assembly of claim 1, wherein the plurality of fingers define an inner diameter that is adjustable upon rotation of the body.

3. The trocar assembly of claim 2, wherein the inner surface of the working chamber is frustoconical.

4. The trocar assembly of claim 2, wherein a diameter of the surgical tool is smaller than an inner diameter of the cannula, and wherein the inner diameter of the plurality of fingers is adjustable to support and center the surgical tool within the cannula.

5. The trocar assembly of claim 2, wherein the body is coupled to the trocar housing at a threaded interface, and the tool stabilizing device is actuated by rotating the body relative to the trocar housing via the threaded interface.

6. The trocar assembly of claim 5, wherein a pitch of the threaded interface corresponds to a predetermined amount of rotation of the body to adjust the inner diameter to a predetermined magnitude.

7. The trocar assembly of claim 5, wherein the tool stabilizing device further comprises a gripping interface that provides a location to engage and rotate the body relative to the trocar housing.

8. The trocar assembly of claim 1, further comprising a lubricious material coated on the plurality of fingers to mitigate drag against an outer surface of the surgical tool.

9. The trocar assembly of claim 1, further comprising:
 a first marking provided on the trocar housing;
 a second marking provided on the body and alignable with the first marking by rotating the body, wherein aligning the first and second markings alters an inner diameter of the plurality of fingers to a predetermined magnitude.

10. The trocar assembly of claim 1, wherein an inner diameter of the plurality of fingers is the same as an inner diameter of the cannula when the plurality of fingers are in the relaxed state.

11. A method of using a trocar assembly, comprising:
 introducing a surgical tool into a working chamber defined by a trocar housing, wherein the working chamber communicates with a cannula coupled to the trocar housing, and wherein a tool stabilizing device is coupled to the trocar housing and includes an annular body received within the working chamber and a plurality of fingers extending distally from the body and radially inward toward a centerline of the body in a relaxed state;
 extending the surgical tool through the tool stabilizing device and into the cannula;
 rotating the body relative to the trocar housing in a first direction to engage the plurality of fingers against an inner surface of the working chamber and thereby flexing the plurality of fingers radially inward from the relaxed state;
 stabilizing and centering the surgical tool within the cannula with the plurality of fingers; and
 rotating the body relative to the trocar housing in a second direction opposite the first direction and thereby disengaging the plurality of fingers from the inner surface and allowing the plurality of fingers to elastically return to the relaxed state.

12. The method of claim 11, wherein the trocar housing defines a frustoconical inner surface within the working chamber, and wherein adjusting the inner diameter of the plurality of fingers comprises:
 engaging the plurality of fingers against the frustoconical inner surface; and
 radially collapsing the plurality of fingers to decrease the inner diameter of the plurality of fingers.

13. The method of claim 11, wherein the body is coupled to the trocar housing at a threaded interface and actuating the tool stabilizing device comprises rotating the body relative to the trocar housing via the threaded interface.

14. The method of claim 13, wherein the tool stabilizing device further comprises a gripping interface and actuating the tool stabilizing device further comprises:
 engaging the gripping interface; and
 rotating the body relative to the trocar housing at the gripping interface.

15. A trocar assembly, comprising:
 a trocar housing that defines a working chamber;
 a cannula extending from the trocar housing at a proximal end to facilitate communication between the cannula and the working chamber, the cannula defining a plurality of fingers and each finger provides a tapered outer portion; and
 a tool stabilizing device coupled to at least one of the trocar housing and the cannula and actuatable by rotation to stabilize and center a surgical tool within the cannula, the tool stabilizing device including:
 a body arranged about an exterior of one or both of the trocar housing and the cannula; and
 a ring arranged at and integral to a distal end of the body and having an annular shoulder engageable with the tapered outer portion of each finger to adjust the plurality of fingers radially inward when the tool stabilizing device is actuated;
 wherein the plurality of fingers define an inner diameter that is adjustable upon actuation of the tool stabilizing device.

16. The trocar assembly of claim 15, wherein the body is coupled to the exterior of the trocar housing or to the cannula at a threaded interface, and the tool stabilizing device is actuated by rotating at least a portion of the body relative to the trocar housing or the cannula via the threaded interface and thereby moving the ring relative to the tapered outer portion of each finger.

17. The trocar assembly of claim 16, wherein a pitch of the threaded interface corresponds to a predetermined amount of rotation of the portion of the body to adjust the inner diameter to a predetermined magnitude.

18. The trocar assembly of claim 16, wherein the portion of the body comprises a gripping interface coupled to the body at an annular groove.

19. The trocar assembly of claim 15, wherein the annular shoulder biases the plurality of fingers radially inward to reduce the inner diameter of the cannula when the tool stabilizing device is actuated.

* * * * *